Figure 1:
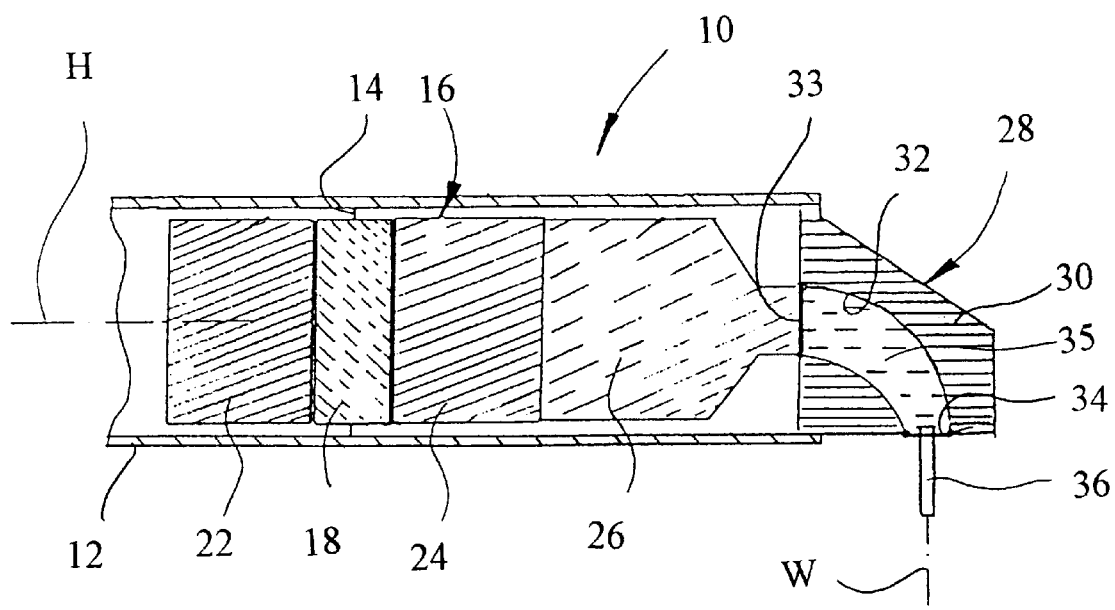

United States Patent [19]

Hahn

[11] Patent Number: 6,139,320
[45] Date of Patent: Oct. 31, 2000

[54] APPARATUS, METHOD AND EXPEDIENT MATERIALS FOR ULTRASONIC PREPARATION OF HUMAN AND ANIMAL HARD OR SOFT TISSUES AND OF DENTAL OR BONE REPLACEMENT MATERIALS AS WELL AS OBJECT OBTAINED THEREBY

[76] Inventor: Rainer Hahn, Stäudach 34, D-72074 Tübingen, Germany

[21] Appl. No.: 08/700,543
[22] PCT Filed: Feb. 27, 1995
[86] PCT No.: PCT/EP95/00710
   § 371 Date: Aug. 28, 1996
   § 102(e) Date: Aug. 28, 1996
[87] PCT Pub. No.: WO95/22938
   PCT Pub. Date: Aug. 31, 1995

[30] Foreign Application Priority Data

Feb. 27, 1994 [DE] Germany .................................. 4406323

[51] Int. Cl.⁷ .............................. A61C 1/07; A61C 3/03; A61C 3/08
[52] U.S. Cl. .................. 433/119; 433/86; 433/88
[58] Field of Search .................................. 433/119, 86, 88

[56] References Cited

U.S. PATENT DOCUMENTS

| 2,947,082 | 8/1960 | Epstein | 433/119 X |
| 3,401,690 | 9/1968 | Martin | 433/119 X |
| 3,924,335 | 12/1975 | Balamuth et al. | 433/119 |
| 4,162,576 | 7/1979 | Takemoto et al. | 433/119 X |
| 4,332,558 | 6/1982 | Lustig | 433/119 X |
| 5,772,434 | 6/1998 | Winston | 433/119 |

*Primary Examiner*—Nicholas D. Lucchesi

[57] ABSTRACT

For ultrasonic preparation of hard or soft tissues or of tissue replacement material a apparatus is proposed comprising a hand piece (10), which includes an ultrasonic vibration generator (16), an ultrasonics deflecting head (28) as well as a tool (36) carried by the output member of the deflecting head. An abrasive treatment medium (48) is supplied to the working region defined between the tool (36) and the material (66) to be prepared. Thus even in places, which are difficult to access, cavities can be produced in dental or bone tissue in a gentle and precise manner.

65 Claims, 12 Drawing Sheets

APPARATUS, METHOD AND EXPEDIENT MATERIALS FOR ULTRASONIC PREPARATION OF HUMAN AND ANIMAL HARD OR SOFT TISSUES AND OF DENTAL OR BONE REPLACEMENT MATERIALS AS WELL AS OBJECT OBTAINED THEREBY

The present invention relates to an apparatus, a method and expedient materials for ultrasonic preparation of human and animal hard or soft tissues, particularly dental and bone materials, and of artificial replacement materials as they are used for the reconstruction of teeth or bones. The invention further relates to objects obtained thereby.

Subtractive treatment of natural hard tissues, as e.g. dental enamel, dental bone, dental cement and bones as well as of tooth or bone replacement materials is the basis of almost any dental or surgical intervention. Up to date the treatment of the said hard tissues is carried out in every day work using rotary diamond or hard metal tools or by use of sharp, e.g. chisel shaped manual tools.

The use of such work tools results in pronounced vibrations, production of unpleasant noises and induction of partly considerable pains. There is the danger of excessive heating of the vital tissues treated which may result in irreversible damages of the organic components and adjacent organs, e.g. tooth pulp. In addition it is impossible to selectively cut off material, e.g. dental hard material, e.g. cariously degenerated dental hard substances while saving adjacent healthy tissue. In the cutting action of the tool formation of craters and fractures in the brittle inorganic components of the tissue or the tissue is not rare, e.g. also including possible chipping off of the dental enamel jacket from the tooth bone during treatment of the enamel using rotary diamond tools. In addition the minimum ratio between cross section and length of the tools required for obtaining the minimum stiffness necessary for a particular application impedes the handling of the tools in regions, which are difficult to reach, e.g. in thin elongates cavities, endodontic cavities and surface portions extending along the tooth roots or therebetween. Last but not least there is a high risk of injuring adjacent soft tissues by rotary cutting tools by inadvertant sliding off, e.g. of manually operated tools.

The geometry of the cavity obtained is the result of the geometric form of the e.g. rotary tool as well as of the relative moment between the tool and the workpiece; preparation of standard geometric shapes is not possible.

Preparation of cavities specific for a particular indication is carried out in accordance with predetermined basic rules (experts' knowledge), which, however, due to the individually produced shapes of the cavities cannot be used as "informations" for producing e.g. tooth or bone restoring parts. Thus making reconstructions requires a precise modelling of all the treated surfaces; smaller errors in the imaging cannot be corrected by integration of the shape of adjacent precisely modelled surface portions using the knowledge of the expert.

The preparation of vital hard tissues using laser energy will result in thermal damages as well as mechanical damages caused by thermal shocks of the treated hard substances and adjacent tissue, respectively, and such preparation is laborious and not economic as compared to conventional treatment methods.

In addition the preparation of defined cavities is difficult due to the uncontrollable cutting action in the depth coordinate as well as by the non-tactile free handling of the tools. Futhermore there is a danger of injuring the soft tissues by direct radiation and reflection effects, respectively.

Preparation of dental hard tissues using fine alumina grain jet installations is limited to a narrow range of applications and is expensive due to the machining method, due to the hardly controllable handling and due to the fact that a rubber dam must be used. In addition there is a high risk of damaging the lungs of the patient and of the medical staff due to the formation of dust, which cannot be avoided.

The preparation of dental and bone tissues using oscillating tools has already been described decades ago.

U.S. Pat. No. 2,874,470 (high frequency dental tool, 1959) discloses the preparation of dental hard tissues using magnetostrictive oscillation tools and abrasive liquids.

DE 11 00 424 discloses an amplitude transformer of an ultrasonic drilling device for the treatment of teeth, which transformer is split in a nodal plane of the vibration, which fact facilitates the use of different machining tools.

Electromechanic and magnetostrictive (of the lamella type) transducers for use in the treatment of teeth with oscillating tools and using abrasive liquids are disclosed in U.S. Pat. No. 3,075,288.

Modern ultrasonic treatment tools, which have originated from this state of prior art, comprise e.g. a piezoelectric vibration generator, wherein end mass members of rotational symmetry are coaxially fixed to the two end faces of the piezoelectric quartz for amplifying the vibration by tuning the total system to resonance frequency. In view of amplifying the amplitude end mass members (sonotrodes) of rotational symmetry coaxially fixed to one end of the generator are also useful, which also tuned into resonance oscillation with the vibration generating system, the cross section of which preferably progressively diminishes with increasing distance from the piezoelectric quartz. A further end mass member tuned to resonance frequency and representing a work tool can be coaxially connected to the end face of the sonotrode.

The entire system is in a state of harmonic longitudinal vibrations along its longitudinal axis, the largest amplitudes being obtained at that one of the end faces of the vibration amplifyer being remote from the piezoelectric quartz and the system showing at least one nodal plane being perpendicular to the longitudinal system axis (=longitudinal axis of the vibration generator) and extending through the center of the piezoelectric quartz.

Operation of the above tooth treatment tools in the ultrasonic frequency region (about 18 kHz to 30 kHz) due to the physical relations between the resonance frequency and the wave length results in sufficient operating amplitudes of the preferably metallic tool, around which a liquid is made to flow, and thus causes cavitation effects causing machining of material, particularly for removal of dental tartar. On the other hand the wave length of the ultrasonic treatment tool operated in resonance determines the structural dimension of the tool in the direction of the longitudinal axis of the system and thus is not favourable for using the tool in regions, which are difficult to acces. Particularly treatment of lateral teeth can hardly be carried out using prior art ultrasonic treatment tools because of the physiologically limited mouth opening of about 40 to 50 mm.

In view of finding a solution to this problem the firm Cavitron Ultrasonics in 1956 (U.S. Pat. No. 492,924) has described tools for ultrasonic treatment of dental hard substances, which are characterized by an eccentric distribution of the mass with respect to the longitudinal axis of the system. Such tool are also disclosed in DE 1 258 017, U.S. Pat. No. 2,990,616 and a scientific paper by H. H. Postle published in J.Prosth.Dent.Vol.8, 1958, pages 153–160. Vibrational excitation of the tools, which have an eccentric distribution of the mass, along the longitudinal axis of the system results in the induction of transversal, particularly ellipsoidal spacial vibrations of the treatment tool, so that there is a component of the amplitude in each of the spacial directions. However, the component of this amplitude along the direction of preparation, which generally is perpendicular to the longitudinal axis of the system (axis of the handpiece) is not sufficient for producing cavities in teeth. The spacial vibrations also prevent the formation of a continuous film of liquid between the tool and the surface to be treated, which, however, is a prerequisite for transfer of energy and machining of material, e.g. by cavitation effects.

Furthermore, the uncontrollable, partly high amplitudes in the various spacial directions cause mechanical damaging of the partly brittle dental hard tissues (H. Sprange and G. Haim, ZWR Vol. 22 1969, pages 1028–1031). In addition removal of dental plaque by such ultrasonic tools, which even today are still in use without substantial modfications, results in significant roughening of the treated tooth surfaces, which favours the formation of new plaque. Last but no least the high amplitude bears the risk of thermal damaging of hard and soft tissues.

The use of e.g. dental ultrasonic tools under continous cooling by water is thus limited to the removal of supragingival dental tartar. Up-to-date an application for preparing defined cavities, for cleaning subgingival tooth surfaces, particularly those located in pockets of the gingiva, for desirable cutting treatment of endodontic cavities as well as for treatment of dental and bone replacement materials is not possible up-to-date.

Ultrasonics driven rotating tools using conventional cutting work tools (diamond tools with bound grains or cutting hard metal tools) are disclosed in U.S. Pat. No. 4,281,987, U.S. Pat. No. 4,289,149 as well as in a review paper by L. Balamuth, IEE 1963, pages 96–101. The machining mechanisms do not differ from conventional rotary (air driven or motor driven) tools, the ultrasonic drive being comparatively uneconomic.

AT 290 005 discloses a device for reproducibly machining teeth using a "stationary" sleeve, which seems to be under the influence of an "ultrasonic field". The "ultrasonic field" is not described in more detail, although the graphical representation joined represents the handling of the sleeve in the region of lateral teeth.

Using the known ultrasonic treatment devices known up-to-date due to the above mentioned physical principles it is not possible to create in such a sleeve longitudinal work amplitudes being parallel to the longitudinal axis of the tooth which are effective in this sense of chipping material, particularly in the region of lateral teeth. In such an application lateral and spacial vibrations would result in a superposition of the vibration geometry and the standard tool geometry, thus resulting in massive imaging errors in the sinking in of the sleeve. A reconstruction using standard crowns, which have been prefabricated in analogy to the shape of the sleeve, is impossible, when there are spacial vibrations of the treatment tool or the sleeve, since the geometry of the vibration will result in geometric discrepancies between the treated surfaces of the tooth stump and the interior surfaces of the restoration.

On the other hand the use of standard tools as the sleeve mentioned above or the tool disclosed in U.S. Pat. No. 2,874,470 for preparing the total cavity of an inlay does little to save the substance of a tooth, since teeth have individual geometries and varying individual dimensions. Furthermore there is no safety e.g. as to complete removal of sick portions of the tissue. Last but not least there is the danger of inadvertant opening of adjacent, e.g. endodontic cavities.

The object of the present invention is thus to provide an ultrasonic treatment apparatus, wherein at the tool work amplitudes are obtained which are effective in view of maching material, which has a considerable shorter length than prior art ultrasonic treatment instruments and can be handled in an ergonomically favourable way like a prior art angled hand piece, thus allowing for economic use of such a tool in regions, which are difficult to access, e.g. in the intraoral treatment of hard tissue.

This object is solved by an apparatus in accordance with claim 1.

This apparatus has at least one deflecting head arranged between a vibration generator and a treatment tool, the deflecting head being driven for oscillation in a direction being parallel to the longitudinal axis of the vibration generator and providing a driving motion in the longitudinal direction of the treatment tool, the longitudinal axis of the vibration generator and the longitudinal axis of the treatment tool including an angle being different from 0°.

Such deflecting heads can even be produced with substantially smaller height than the vibration generating system itself, which fact further facilitates handling of the treatment tool.

The geometric shape of the deflecting head modifying the direction of the ultrasonic oscillation is formed specific to the particular application. If it is a deflecting head comprising a vibrating member showing a plurality of maxima of the vibration, these maxima corresponding to the driven part and the driving part of the deflecting head, the geometric shape together with the material(s) determines its eigenfrequency as well as the form of the vibration induced in the direction of the treatment tool.

Materials, which are particularly suited for providing solid state resonating members for deflecting heads are elastic materials, preferably metallic materials, particularly C-steel materials of preferably martensitic or bainitic structure, which particularly preferred are surface treated and/or conditioned, or titanium or bronze alloys.

The geometric shape of solid state resonating members should allow for an elastic oscillation thereof in resonance with the vibration generating system, the resonating member deforming in longitudinal direction of the vibration generating system, preferably with no phase shift, and also oscillates along directions forming an angle of 60° to 120° with the longitudinal axis of the vibration generating system. Considering the angular displacement between the coordinate directions or using an angled coordinate extending from the vibration generator through the deflecting head to the tool an in-phase motion of the output member of the vibration generator and the tool is obtained.

The treatment tool is mounted on the deflecting head so that it forms an angle of 60° to 120°, particularly preferred of 90° with the longitudinal axis of the vibration generating system. The geometry, length and mass of the treatment tool is chosen so that it oscillates in resonance with the deflecting head and the vibration generating system, respectively.

Spherical, disk shaped or ring shaped deflecting resonating members having a diameter of less than 30 mm, preferably less than 20 mm are particularly suited for intraoral applications. In view of improvement the efficiency hollow spherical, ring shaped or in particular cylindrical sleeve shaped resonating members have proven.

For connecting the deflecting head to the vibration generating system and for connecting the treatment tool to the deflecting head, the prior art connecting techniques as well as split connections are suitable. Particularly, the deflecting head can be connected to the vibration generating system and the treatment tool can be connected to the deflecting head by soldering, welding, adhering, screwing, bracing, wedging or by means of friction cones. In this respect the combination of a threaded connection and a friction cone has shown to be particularly satisfactory. Of course, the vibration amplifier of the vibration generating system and the deflecting head and/or the treatment tool and the deflecting head may also be made as a one piece construction. Generally, the connections are made in a symmetry plane of the deflecting head defined by the axis of the vibration generator and the tool axis.

As has been found out, liquid volumes or high pressure gas volumes or combination of both these systems being sealing contained in curved deflection channels surprisingly are also suited for deflecting ultrasonics. Preferably the sealed liquid and/or gas system is formed such that the liquid or gas volume is driven into oscillation, particularly resonance oscillation with the latter by excitation parallel to the longitudinal axis of the vibration generating system. The oscillation of the liquid or gas volume thus produced will then be transferred to a treatment tool, which by adjusting its length, geometry and mass is tuned to resonance frequency, preferably without inducing phase shifts (curved coordinate extending along the axis of the deflecting channel).

Volumes of a liquid and/or high pressure gases are particularly useful, which are sealingly confined between an entrance opening and an outlet opening of the curved deflecting channel of a sealed housing, sealing being obtained by means of a diaphragm or by means of a movable plunger. The housing is shaped specific to the respective application, the walls of the housing not being driven into oscillation, particularly not into resonance oscillation by the osciallation of the column of liquid.

Up to the mark are media, which when exposed to ultrasonics are liquids, particularly low viscous liquids, as e.g. aqueous or alcoholic solutions, oils, particularly silicone oils and synthetic oils, polymers, quicksilver, low melting nickel alloys or highly compressed volumes of gases, particularly inert gas volumes of preferably more than 10 bar pressure, particularly preferred pressures being such of more than 50 bar. In the case of liquids which incorporate gases like water, the liquid is degassed before being sealed into the deflecting channel.

For intraoral applications fluid tight stainless metallic housings of the deflecting head and volumes of liquid of about 0.1 ml to 30 ml, particularly 0.5 ml to 5 ml have proven, which are sealed by respective elastic diaphragms, especially metallic diaphragms, preferably made from surface hardened spring steel. The two elastic diaphragms communicate via the filling volume of the liquid and/or the gases.

For connecting the diaphragms to the vibration generating system and the treatment tool, respectively, all of the above described connecting and jointing methods can be used, the diaphragms eventually being formed with a flange on that face thereof being remote from the filling volume. It is also a success to connect the diaphragms in centric manner (with regard to the longitudinal axis of the vibration generating system and the treatment tool, respectively) to the respective end faces of the vibration generating system and the treatment tool, respectively. Of course, at least part of the end face of the vibration generating system and/or the treatment tool can also be used as a diaphragm.

Particularly well suited are diaphragms which are arranged perpendicular to the longitudinal axis of the vibration generating system and the treatment tool, respectively. For improving the vibration characteristics of the deflecting head diaphragms are particularly suitable, the thickness of which continuously decreases from the periphery thereof (fixing to the housing of the deflecting head) towards the center thereof. For simple adjustment of the resonance condition it is particularly useful to use qualitatively identical diaphragms for the input diaphragm and the output diaphragm.

For optimum oscillation of the communicating diaphragms and the column of liquid, respectively, the diameter of the diaphragm should at least slightly exceed the cross section of the respectively coupling end faces of the vibration generating system and the treatment tool, respectively, the ratio of the diameters of input diaphragm and output diaphragm directly influencing the ratio of amplitudes of the input and output oscillations. In view of amplifying the amplitude of the treatment tool a diameter ratio of input diaphragm and output diaphragm of about 2:1, particularly about 1.5:1 has been well proven.

Such deflecting heads can be built so as to require comparatively little space, and they are easy to clean and sterilize, respectively. In addition the overall metal volume to be elastically deformed is entirely limited to the two diaphragms, by which fact the generation of heat is reduced and the efficiency is increased as compared to solid state-deflecting heads.

Of course the deflecting head can also comprise different communicating liquid or gas volumes or a combination of a solid state-deflecting head and a sealed liquid or gas volume. Particularly, such deflecting heads can comprise low melting alloys having a hard coating, e.g. made from metal, particularly hard metal. Such alloys are solid at ambient temperature, while the influence of ultrasonics will at least partly change their phase state in the sense of rendering them liquid so as to increase the yield of a "solid state" deflecting head.

Suitable treatment tools are in particular metallic tools, e.g. cylindrical, tubular, flame shaped, spherical, bud shaped or conical tools as they are also used in dentistry, preferred tools being, however, free from surface bound grain. The preparation of a cavity is effected by at least partial sinking in of the tool and/or by relative movement between the tool and the surface to be treated. One can also use defined shaping tools which are sinked into the surface to be machined in a direction, which is at least partially parallel to the longitudinal axis of the shaping tool.

Cleaning of teeth is carried out using tools, which have a shape similar to the shape of a golf or hockey bat or which include an extended shovel like work portion and are curved in accordance with the curvature of the tooth.

For coupling energy to the surfaces to be treated, the oscillating tool is continuously flowed around with a liquid or thixotropic gel-type treatment medium, e.g. water or aqueous solutions of chemical agents such that a continous liquid layer is between the tool and the treated surface.

The rapid up and down movement of the oscillating treatment tool will cause cavitation effects in the immediate neighbourhood of the tool, particularly of the end face of the tool, which will result in implosion of cavity bubbles in the liquid filled working gap thus causing chipping surface reshaping of non-metallic materials in the sense of an erosion process. On the other hand the oscillation microchipping treatment of the hard dental materials permits essentially painfree treatment without the need of anesthesy.

The chipping rate becomes smaller with increasing working distance and comes to a standstill upon rupture of the film of liquid. A working distance, which is too small, in combination with the oscillation treatment tool being urged towards the surfaces to be treated under high pressure reduces the production of cavitation effects and will lead to a standstill of the process.

On the other hand applying different manual pressures onto the working tool for urging the latter towards the surface to be treated, the working distance and thus the extent of energy coupling will be varied. This allows for the first time for chipping treatment of a treated surface and gentle finishing or polishing thereof without the need of having to change the tool or provide modifications of the treatment apparatus.

In addition it has been proven to be good to include in the treatment medium fine abrasive hard grain (shortly referred to below by the term abrasive particles) in view of increasing the removal rate. Such abrasive particles are e.g. metal oxide particles, particularly alumina particles, magnesia particles, silicon nitride particles, boron carbide particles, glass particles or fine diamond grain. The grain size of the particles should be about the same order of magnitude as the double of the amplitude of the ultrasonic vibration of the tool, i.e. the total stroke of the ultrasonic vibration of the treatment tool particularly in view of optimum acceleration in the working gap and optimum removal rate resulting therefrom. It has been well proven to use suspensions of abrasive particles the composition of which is characterized by one unit volume of abrasive particles per 30 to 50, preferably 5 to 20 and particularly preferred 10 unit volumes of liquid. The grains are kept suspended, e.g. by continuous stirring or flowing gas through the suspension, e.g. in an exchangeable supply vessel.

As has been found suprisingly the dentin channels opened in the preparation of tooth bone can be sealed during the removal process in the sense of a wound dressing by incorporating fine grain particles (referred to below also by the term sealing particles) into the suspension. Particularly useful to this end is the addition of fine unround metal oxide particles having sharp edges (shortly referred to below by the term ingot shaped), particularly fine alumina particles having an average diameter of less than 3 $\mu$m, particularly of about 1 $\mu$m. Proven mixing ratios are one unit volume of fine grain particles per 2 to 20, perferably about 10 unit volumes of abrasive particles.

Sealing of the dentin channels opened during the preparation, which in accordance with the invention is obtained by fine grain particles, leads to a significant reduction in the permeability of dentin and thus makes unnecessary an expensive wound dressing or a pulp protection.

On the other hand the wedging of the particularly ingot shaped fine grain particles in the treated dentin interface which is resistant to tensile loads, for the first time provides a defined substrate, which avoiding the problematic application of dentin etching solutions and/or dentin bond increasing agents, which gives only a low increase in the bonding quality, can be used to secure adhesion for plastic dental filling materials, particularly polymer composites or glass ionomer cements.

Surprisingly, granulates, which at least partly contain silicates or are silanized or at least partially contain polymers, can make a direct chemical compound with polymerizable dental filling material, eventual displacement of the granulates in the dentin interfaces counteracting the polymerization contraction of the dental filling materials. Furthermore granulates, which at least partly contain silicates, can jelly e.g. with filling cements containing polyacrylic acid.

Supply of the suspension formed by the abrasive particles, the fine grain particles and water (slurry) is effected e.g. by means of nozzles provided at the handpiece or the treatment tool, particularly through an annular nozzle member circularly extending around the treatment tool or through an essentially tubular treatment tool. On the other hand in the case of an exterior supply of slurry the efficiency of removal as well as the visual control can be improved by sucking off medium by means of a tubular treatment tool, particularly in the case of deep cavities.

Alternatively or in addition to aqueous suspensions generally gel-like grain slurries of the above abrasive particles and/or fine grain particles can be used, e.g. suspensions in gels of glycerine or gelatine or 1 to 10% chloro-hexidine-digluconate-gel can be used. The viscosity of such gels can be varied in a way specific to the particular specification, e.g. by addition of aerosiles, makes possible selective application, particularly overcoming gravity, and makes possible to renounce continuous supply of an aqueous abrasive solution and evacuation thereof, respectively. Under the influence of ultrasonics due to the thixotropic character of the gel selective reduction of the viscosity in the immediate vicinity of oscillating tool is obtained, which results in efficient cavitation effects and a sufficient acceleration of the abrasive particles in the working gap.

The use of such gels has been especially proven in regions which are difficult to access, e.g. gum pockets, dental interstices or endodontic cavities. Such gels are also very useful for making tooth restorations and represent an alternative to a continuous supply of an abrasive medium. Of course, the liquids or gels may additionally include chemically active ingredients, e.g. Calcium chelate forming agents (EDTA solution) to chemically assist the removal of hard tissue or sodium hypochlorite solution for disolving remnants of soft tissue, e.g. during the preparation of endodontic cavities, or organic acid solutions for simultaneous removal of smear layers induced by the treatment and/or for micro-morphological restructuration of the treated surfaces or active substances for reducing the number of germs at the treated surfaces and in the surroundings thereof (e.g. reduction of germs in gum pockets), respectively.

So it proved to be good in the selective removal of carious dental hard substances to renounce addition of coarse abrasive particles and to use instead liquids or gels additionally containing e.g. sodium hypochlorite solution.

Of course, liquids of high viscosity e.g. polymer composites can be thixotropically made liquid under the influence of ultrasonics and can be pressed into a thin film between dental cavities and dental restoration parts while being exposed to ultrasonics so as to form the fixing composite.

The defects of hard tissue resulting from cutting removal of carious dental hard substances in dentistry are prepared in the sense of cavities and tooth stumps, respectively in compliance with exact preparing guidelines (expert's knowledge) for improving the stability or the edge position of restoring members to be inserted.

Intraoral cavities, e.g. for receiving insertion fillings or partial crowns can each be subdivided into one or plurality of occlusal cavity segments complying with the expert's knowledge and/or one or a plurality of approximal or buccal or oral cavity segments each having diverging opposing walls.

In accordance with the invention this knowledge of the expert is incorporated into a set of standardized treatment tools of different size gradation, each such treatment tool being formed as the negative model of the cavity segment to be prepared. In particular production of at least one shaping tool for treatment of occlusal cavity segments and/or at least one shaping tool for shaping approximal, buccal or oral cavity segments in at least one size, preferable in different size gradations has proven to be good. The preparation of the cavity is carried out after the individual removal of e.g. carious dental hard substance has been effected, and this preparation is made by sinking in one or a plurality of oscillating shaping tools in accordance with the invention to the preferably pretreated surfaces in a direction being parallel to the longitudinal axis. Combined geometries of a cavity result from adjacent sinking in of different segment tools, particularly after preselection among suitable sizes of shaping tools.

The restoration of such cavities, in accordance with the present invention is carried out by inserting of at least one standardized mating member or filling member having the same geometry as the treatment tool(s) used, which mating or filling member is selected from a set of shaped members corresponding with the respective geometries of the shaping tools as to the shapes and size gradation. More particularly, the use of adhesive restoration methods using polymer composites as well as conditioning of the surfaces of the cavity walls and of surfaces of the filling members or surfaces of the cavity or surfaces of adjacent filling member segments in a way being specific for the material, has been proven to be good. Thus preparation of the cavity and final restoration is carried out in the same treatment session avoiding complicated modelling techniques as well as the expensive production of individual mating members in a laboratory.

Still furthermore shaping tools in accordance with the present invention can also be used in the preparation of surface segments, particularly the surfaces of tooth stumps, e.g. in connection with the preparation of veneer shells or of crown stumps. Again the knowledge of the expert relating to the shaping of the stump surfaces extending essentially parallel to the longitudinal axis of the tooth is put into a set of essentially shovel shaped preparation tools of different size gradations and different radii of curvature. Particularly the knowledge of the expert relating to preparation of edge transisions, particularly of the edges of crowns, e.g. in the form of stepped transitions or flute transitions each with or without edge chamfer can be put into a shaping treatment tool, which at least partially is formed as the negative of the surface geometry to be produced. The preparation of edge transisions preferably is made by circular guiding of such tools parallel to the longitudinal axis of the shaping tool along the entire edge transition to be reshaped or to be finished. This method has proven to be particularly useful, since eventual imprecision in the production of models can be integrated as to the geometry by integrating into the geometry the geometry of adjacent precisely modelled surface sections of the model stump additionally considering the expert's knowledge, which integration is preferably carried out by reworking of the model stump using identical shaping treatment tools.

The use of a set of tools designed in analogy to the surfaces of the dental roots or surface segments thereof, which e.g. may have the shape of a scoop or a golf or hockey bat, also allows to remove tooth plaque and adsorbed hard substances, e.g. dental tarter from supragingival and subgingival root surfaces, the composition of the working medium used (e.g. water or an abrasive suspension) as well as the vibration mode of the tools allowing for an essentially selective removal of dental tarter and eventually of concrements without the danger of major volumes of healthy dental hard tissue being removed or being modified e.g. in the sense of a surface roughening.

Futhermore use of at least partially oval treatment tools for the first time allows to prepare endodontic cavities according to their form, which in analogy to the cross section of the root normally is oval, using an instrument.

Surprisingly, it was further found, that essentially wire shaped, cylindrical or cutting edge shaped treatment tools e.g. made from chrome and nickel containing metal alloys when exposed to ultrasonics and not cooled by water are selectively heated by internal friction effects and can be used for cutting treatment of soft tissues and for coagulation of blood vessels, which have been opened. Such treatment tools are particularly useful, which favour the production of frictional heat when exposed to ultrasonics e.g. due to the fact that they comprise at least two different materials or due to induction of relative movements of the treatment tool with respect to the deflecting head. Using such tools cuts in soft tissue can be made in analogy to $CO_2$ lasers or high frequency electric tools, without occurence of injuries due to undesired optical reflection phenomena or electric sparks.

Heat producing tools can especially be used in endodontics as filing members after having carried out the preparation of a root channel, preferably using treatment tools of same shape. The production of heat allows to use e.g. thermoplastic root filling materials, which are at least partially transferred into the liquid state by the oscillating heat producing tool and which due to forward feeding of the tool in the root channel are pressed into a small volume and which after cooling, which is caused by switching of the ultrasonic oscillation, preferably being adsorbed on the surfaces of the dental hard tissues and the treatment tool fulfill the function of a bonding material (sealer), which closes the individual cavities defined between the dentin walls of the root channel and the treatment tool, which simultaneously serves as a macro-filling member. Cooling of the tool, which due to the conical shape thereof is a directed cooling which is from the tip of the tool to the basis thereof, allows for gap free sealing of the cavities defined between the tool and the wall of the root channel. At the same time the tool after having been detached from the deflecting head is preferably left in the root channel as a geometrically defined shaped member in the sense of a filling member. Preferably the tool is reduced in length corresponding to the individual longitudinal extension of the dental root.

Of course, use of the treatment apparatus in accordance with the present invention and of the methods in accordance with the present invention is not limited to applications in the field of dentistry; they can also be used in equivalent medical and non-medical applications including industrial applications.

Figure 2:
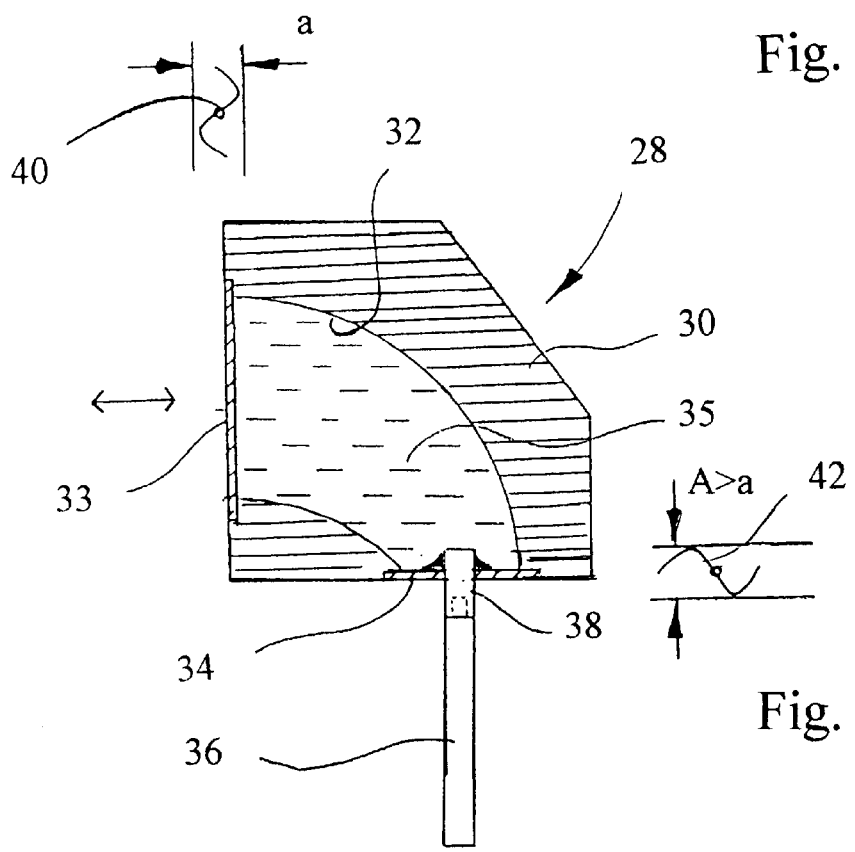
Figure 3:
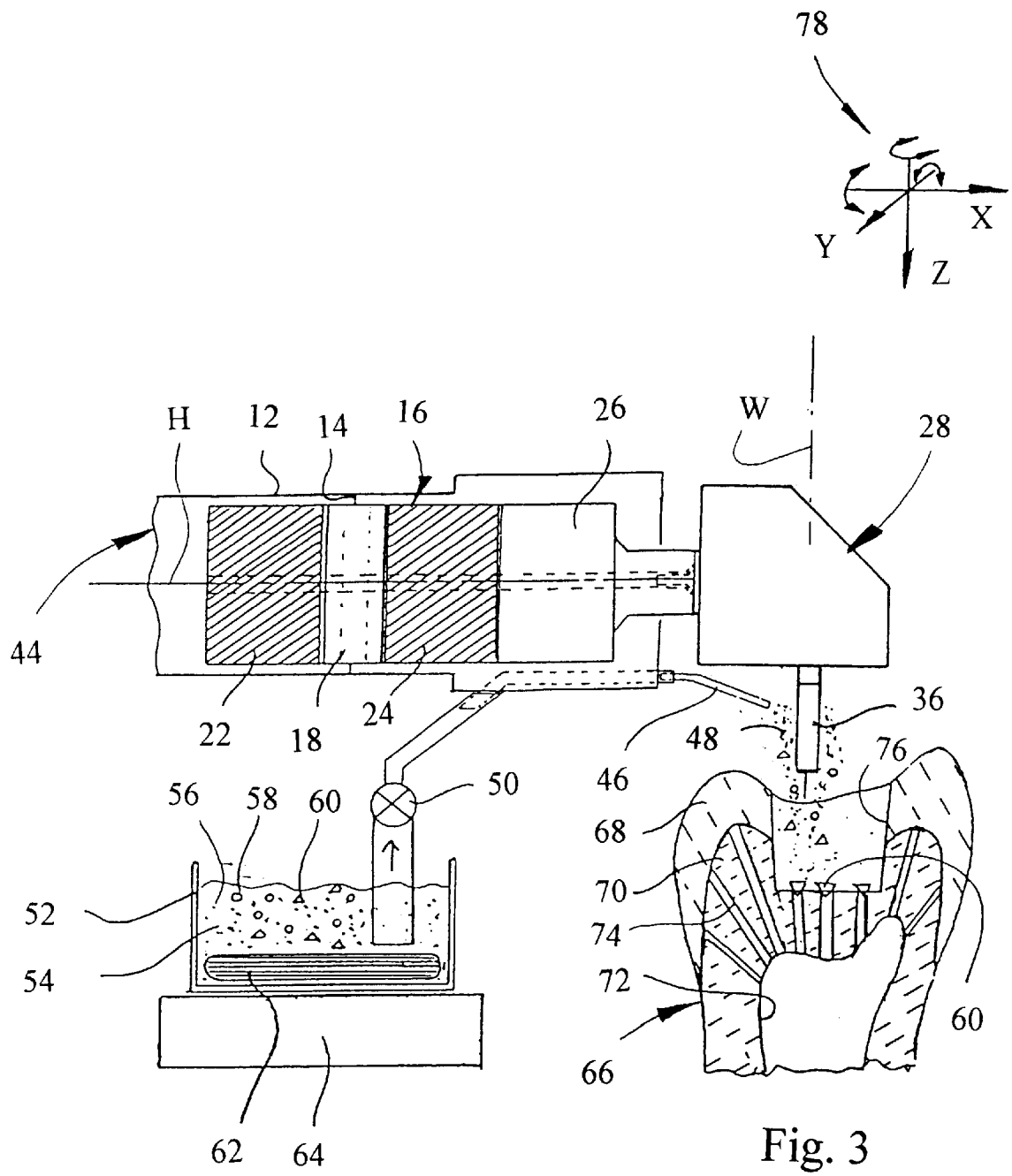
Figure 4:
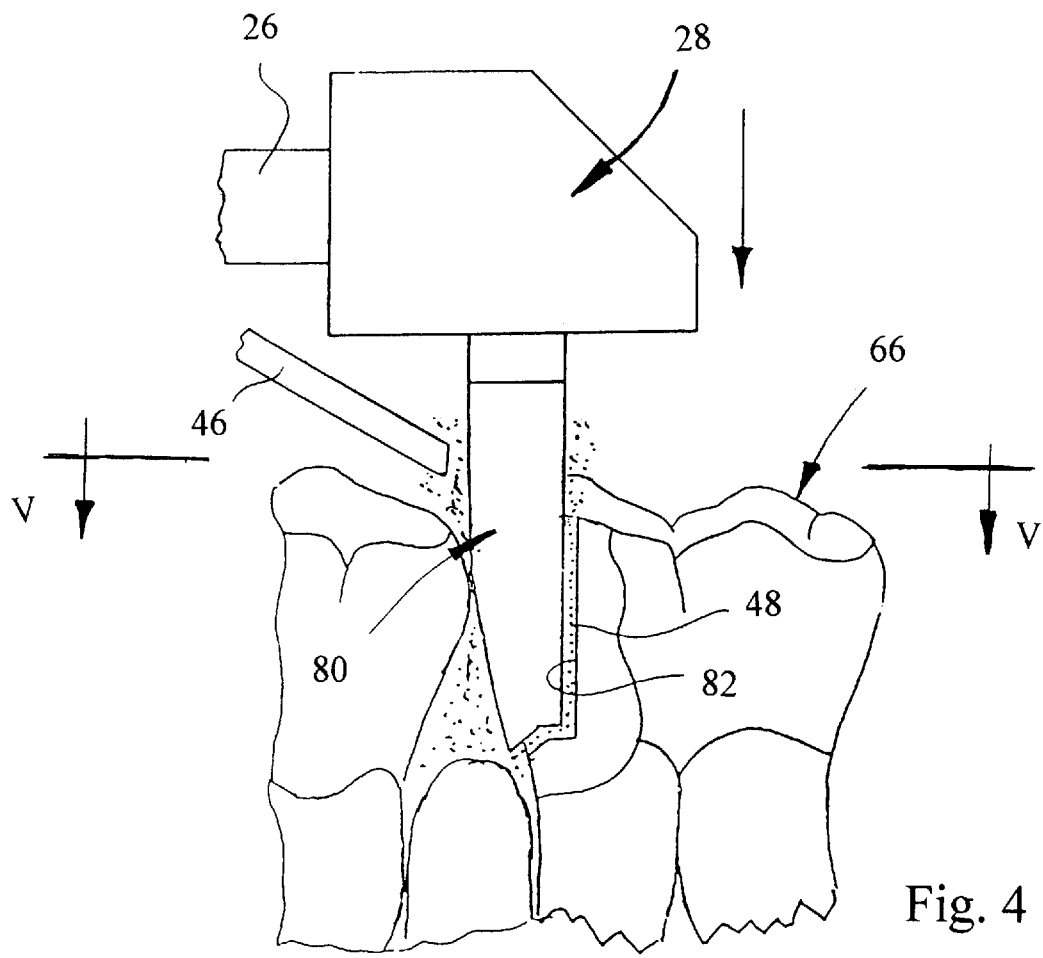
Figure 5:
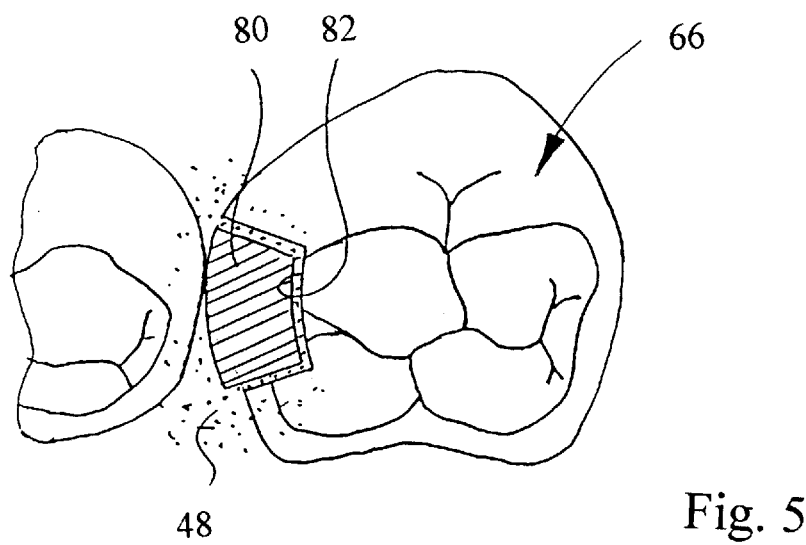
Figure 6:
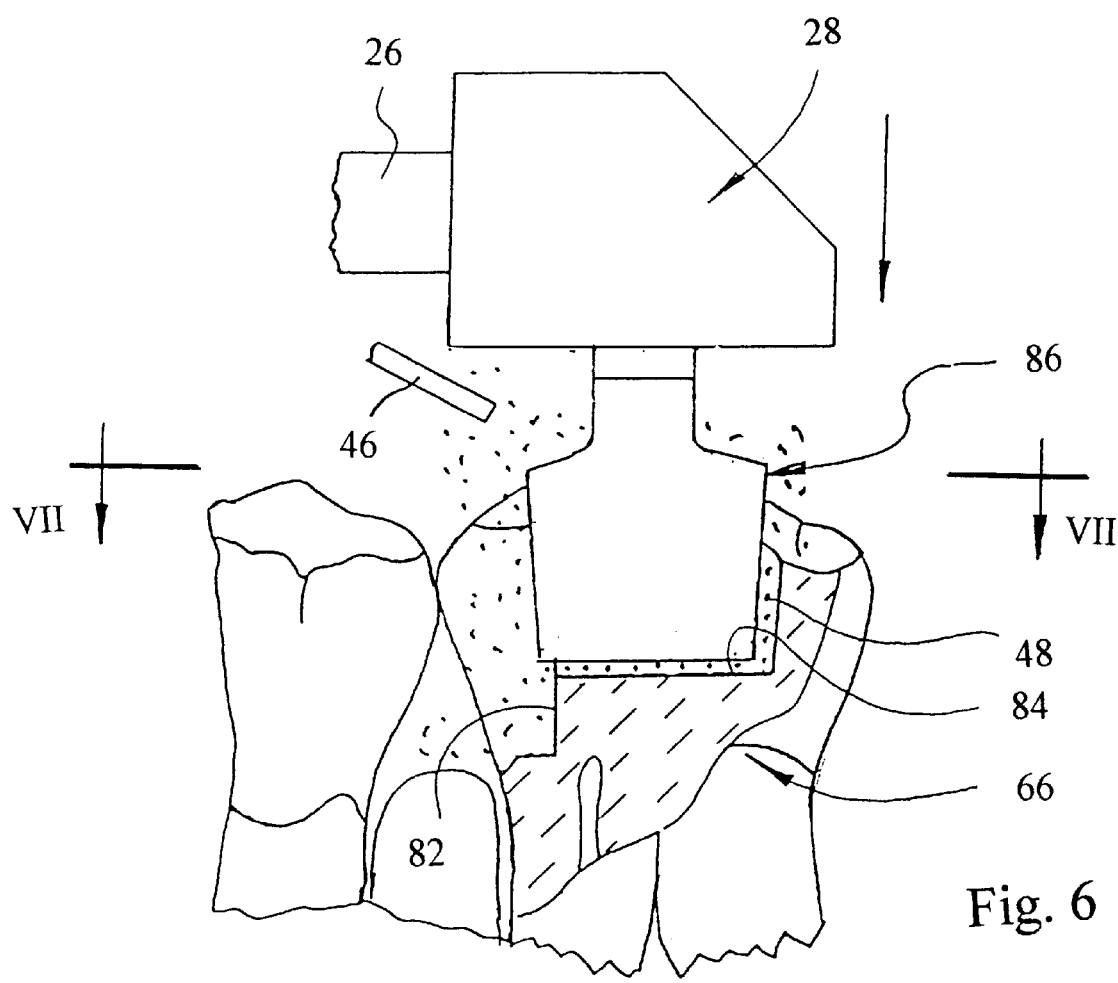
Figure 7:
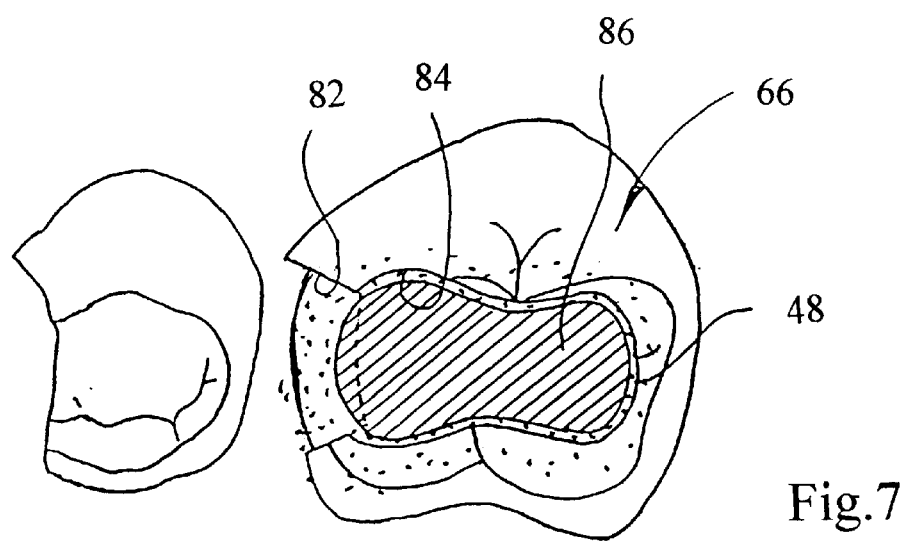
Figure 8:
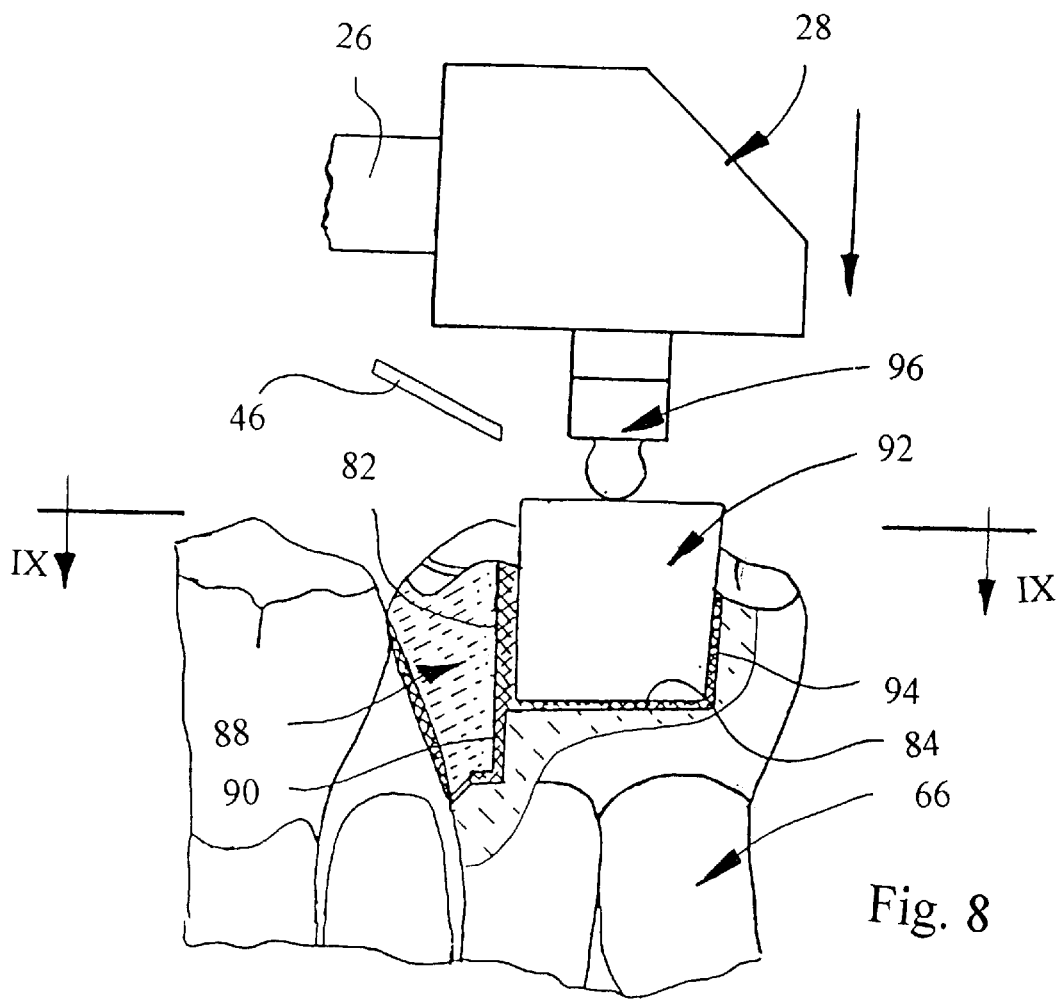
Figure 9:
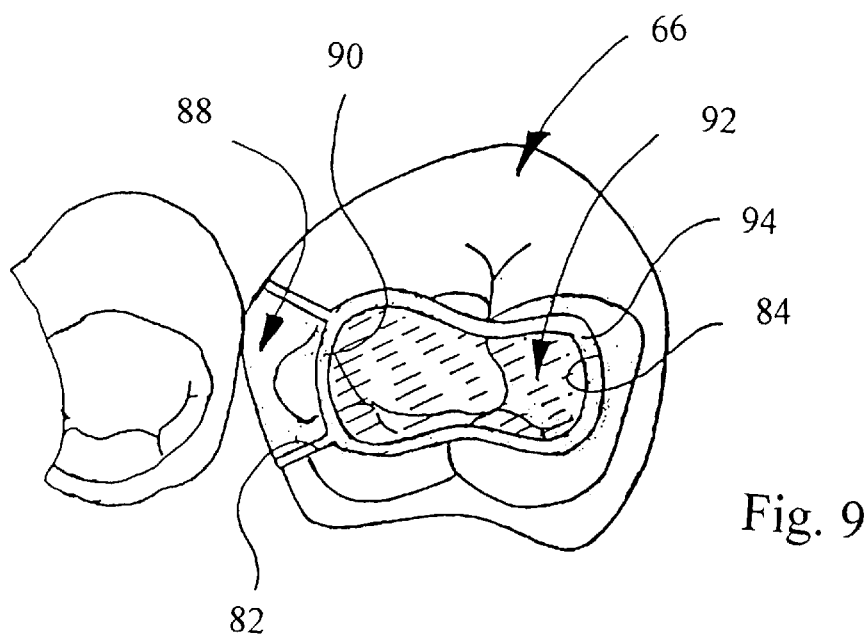
Figure 10:
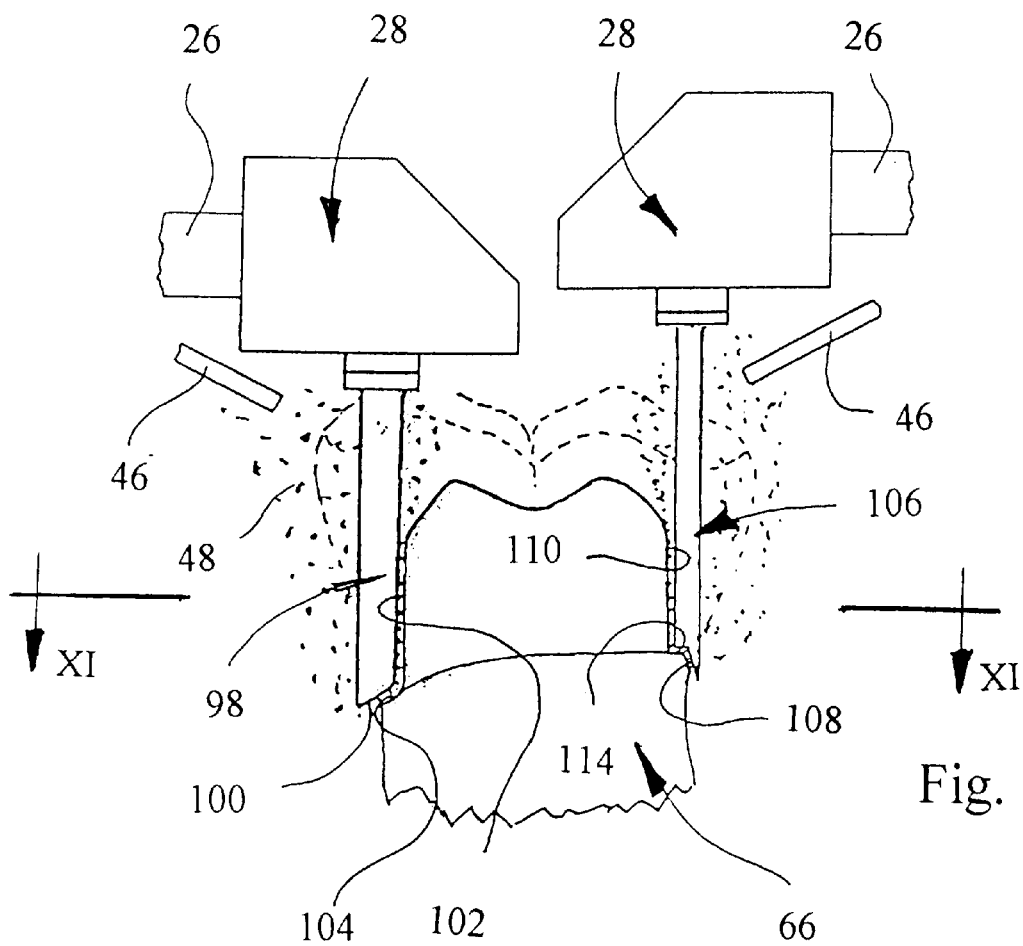
Figure 11:
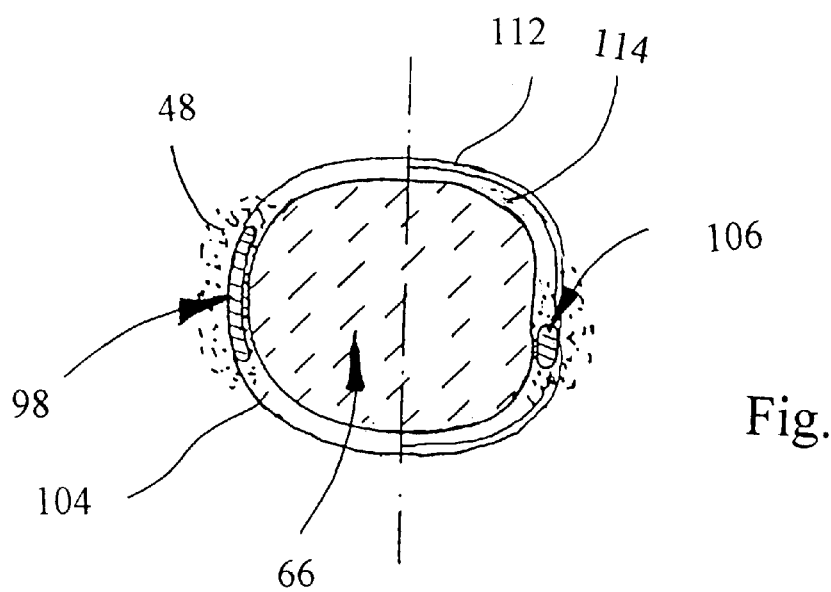
Figure 12:
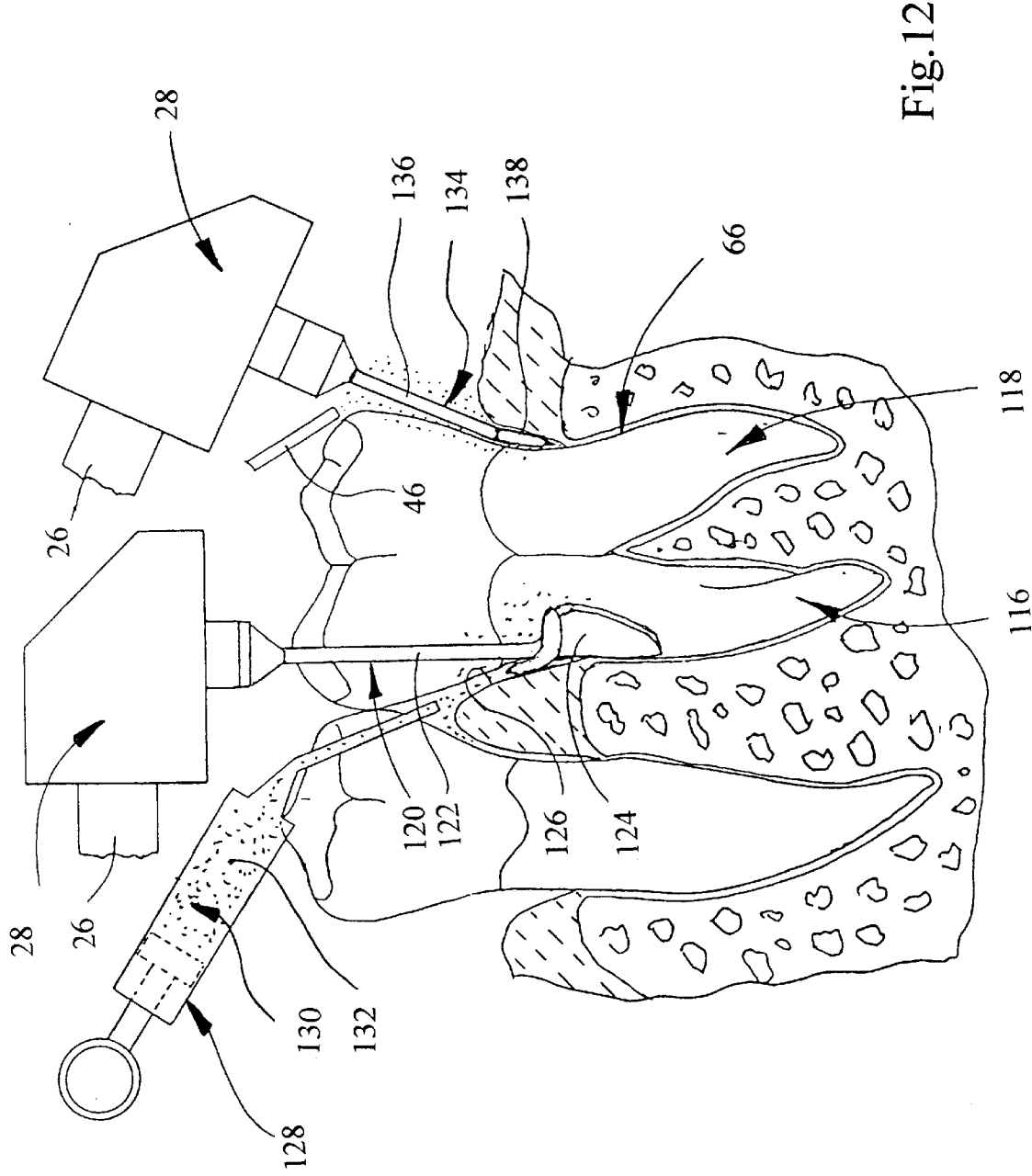
Figure 13:
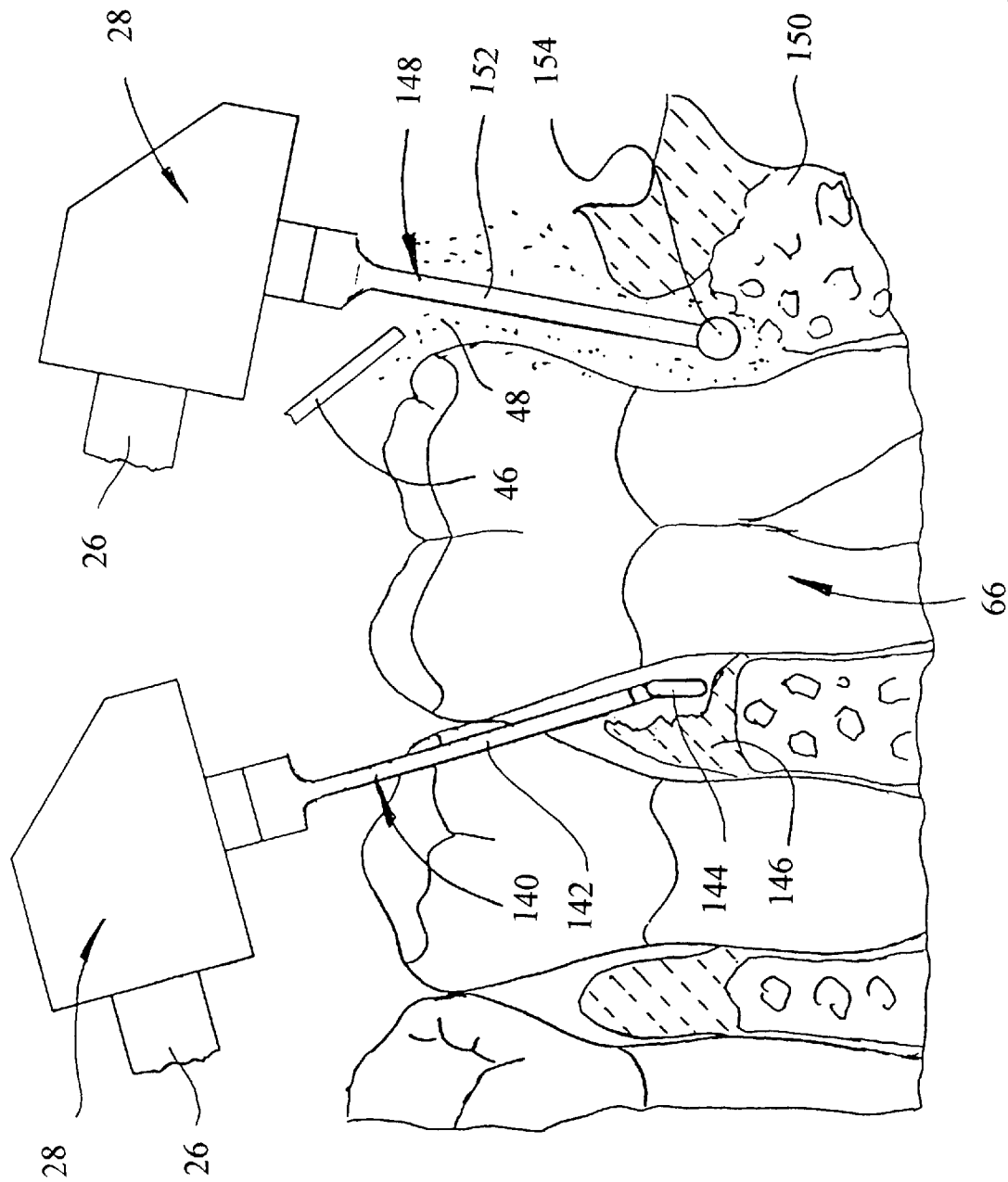
Figure 14:
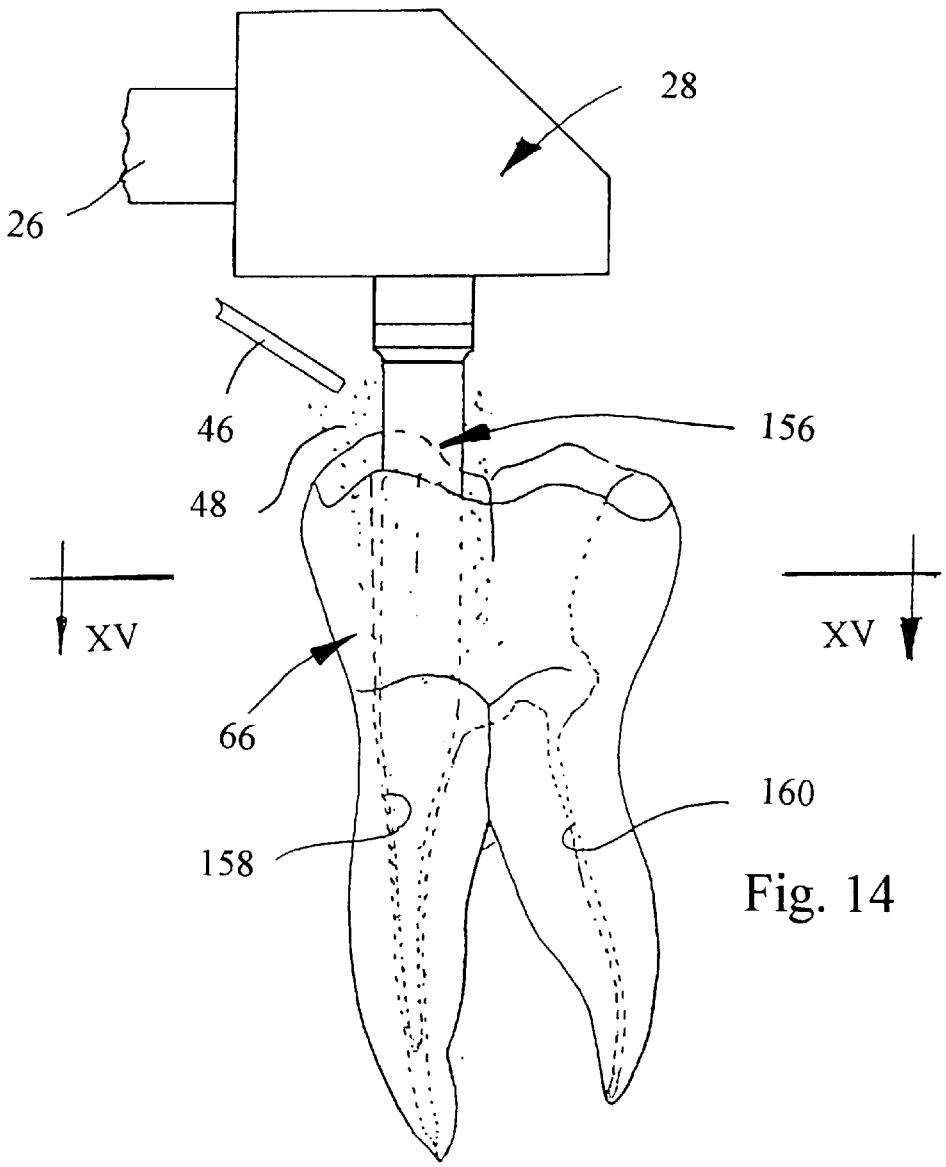
Figure 15:
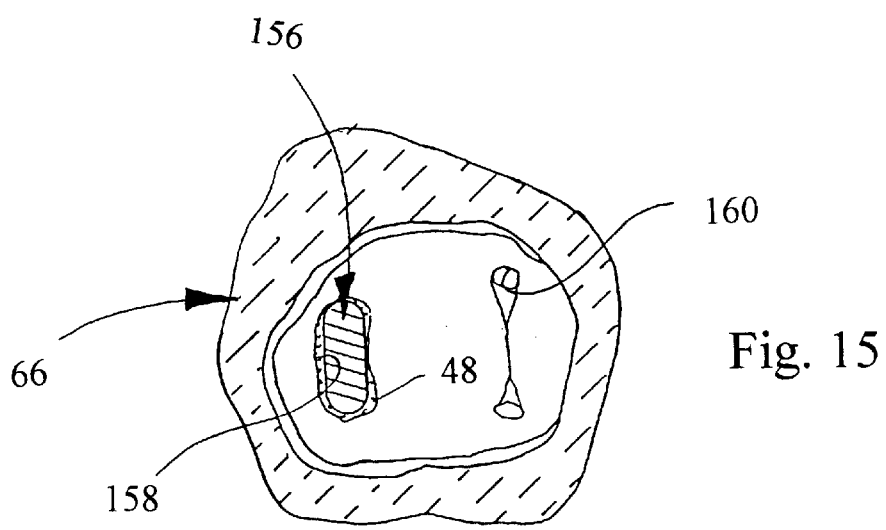
Figure 16:
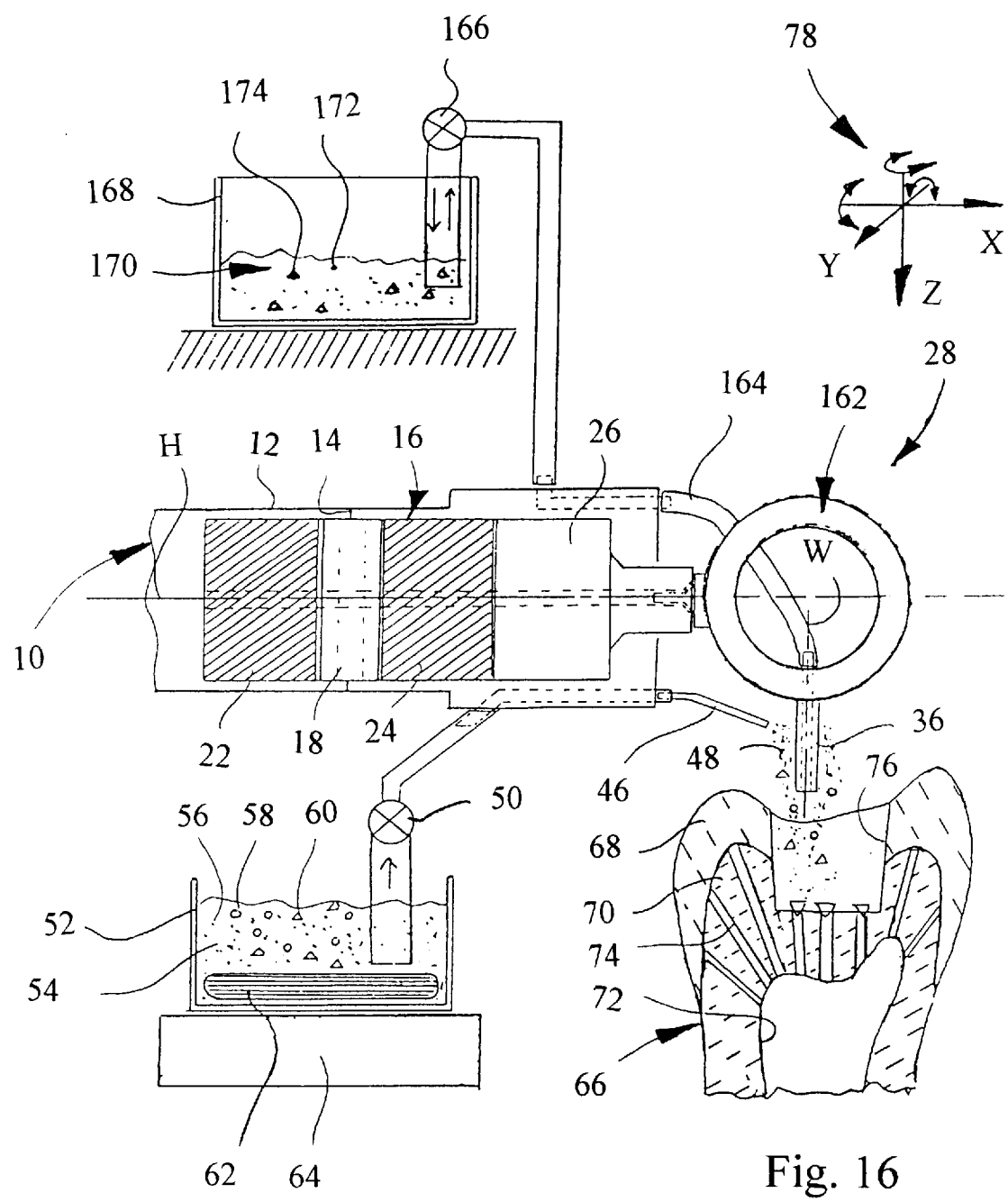
Figure 17:
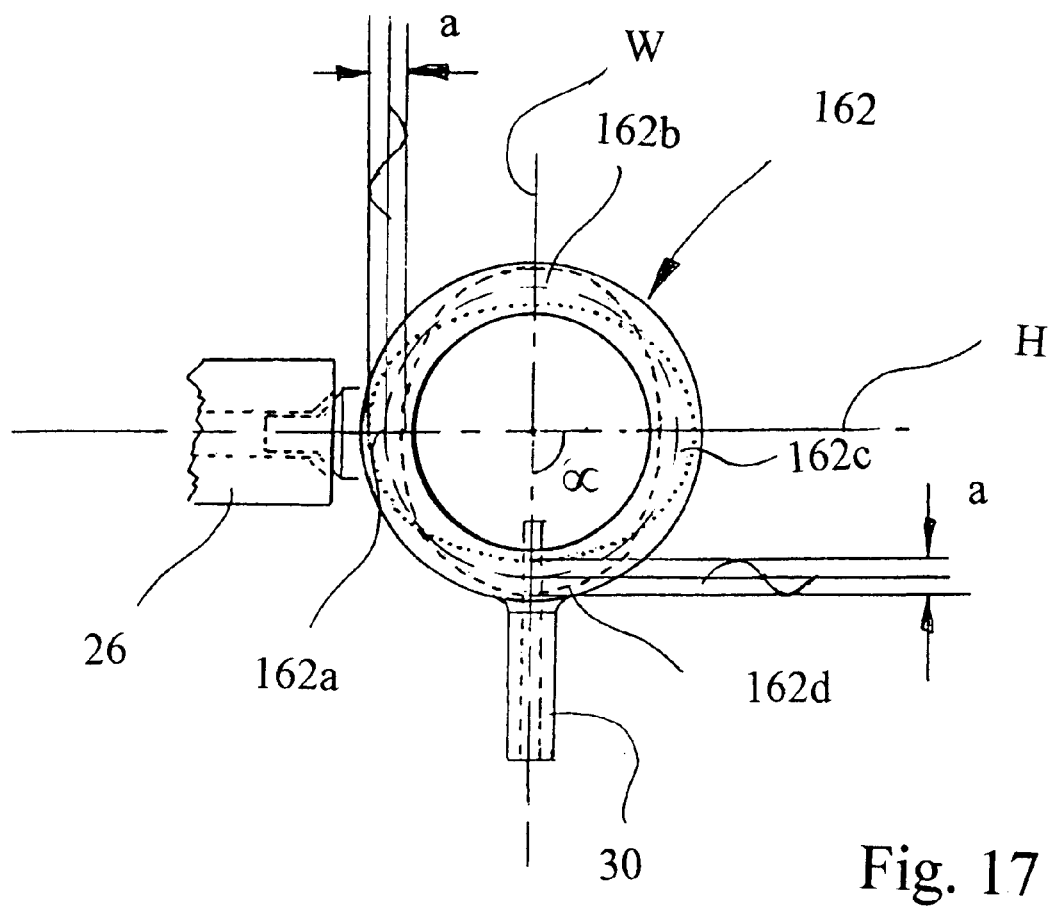
Figure 18:
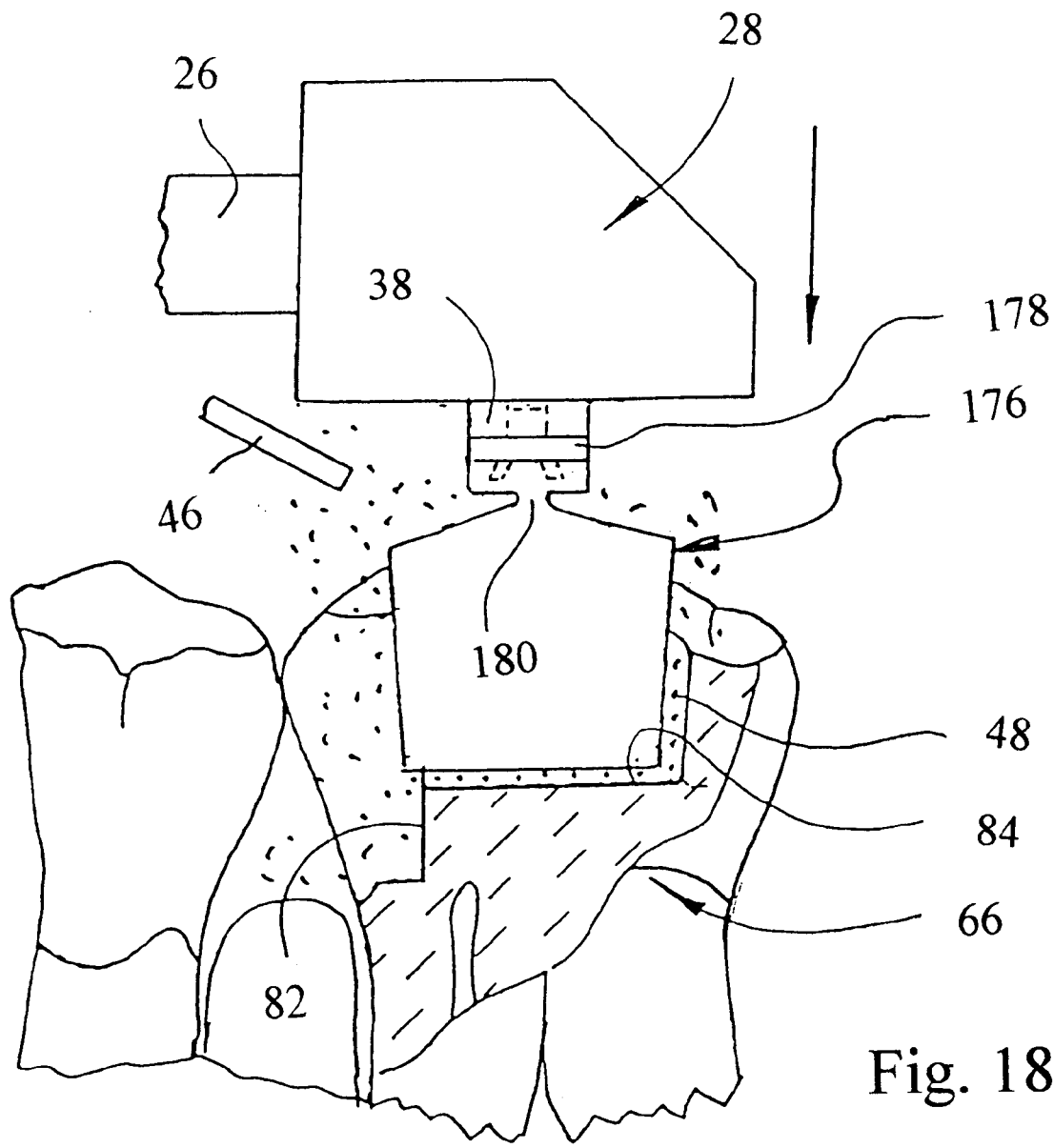

The invention will now be explained in more detail referring to preferred embodiments and to the enclosed drawings. Therein FIG. 1: is an axial section through the end portion of a dental angled hand piece for treatment of dental material;

FIG. 2: is an enlarged section through a sound deflecting unit of the hand piece shown in FIG. 1;

FIG. 3: is a schematic representation of the hand piece of FIG. 1 under operational conditions;

FIG. 4: shows a first step in the preparation of an extended carious region of a tooth using a hand piece in accordance with FIG. 1, seen in*lateral direction, wherein a laterally open recess of the tooth is produced;

FIG. 5: is a section taken along line V—V of FIG. 4;

FIG. 6: is a second step of the preparation following the step shown in FIG. 4, wherein a central recess has been produced in the tooth, as seen in lateral direction;

FIG. 7: is a section along cutting line VII—VII of FIG. 6;

FIG. 8: is a further step in the preparation and restoration in the tooth following the steps shown in FIGS. 4 to 6 and a further step not shown in the drawings and wherein a filling member made from dental replacement material is inserted into the previously created central recess of the tooth, seen in lateral direction;

FIG. 9: shows a section along line IX—IX of FIG. 8;

FIG. 10 is a lateral view of a step as it is carried out for preparing a tooth stump before mounting a crown;

FIG. 11: is a cut along line XI—XI of FIG. 10;

FIG. 12: is a lateral view of a treatment step for treating the upper end portions of the exterior surface of a dental root with an ultrasonic tool;

FIG. 13: shows further dental works using ultrasonic tools, wherein flesh is cut (left portion of the figure) or bone material is removed (right hand portion of the figure);

FIG. 14: is a lateral view of a step of a root channel treatment, which is carried out using an ultrasonic tool;

FIG. 15: is a section along line XV—XV of FIG. 14;

FIG. 16: is a similar representation as FIG. 3, wherein, however, a modified hand piece comprising a solid state sound deflecting unit is shown;

FIG. 17: is a separate representation of the sound deflecting unit of FIG. 16, which will be used for explaining its function in more detail; and FIG. 18: is a lateral view of a preparation of a cavity using an ultrasonic shaping tool, which at the same time serves as a shaped or filling member.

FIG. 1 shows the end portion of a dental angled hand piece generally shown at 10. The hand piece 10 has a tubular housing 12 which also has the function of a grip and in which by means of suspension elements 14 an ultrasonic vibration generator generally shown at 16 is mounted.

The ultrasonic vibration generator 16 comprises a piezoelectric ultrasonic transducer 18, which in turn may comprise a plurality of axially staggered disks made from piezoelectric ceramic material, which disks are mechanically series connected. Mass members 22, 24 of rotational symmetry are arranged on the end faces of the ultrasonic transducer 18, e.g. by being srewed thereon or adhered thereto.

At the end of the mass member 24, which in the drawings is at the right hand end, an amplifying member 26 is provided, which concentrates ultrasonic energy received by its left hand end face towards the free end thereof due to the progressive reduction of its cross section thus providing an ampliofication of the amplitude. Such amplifying members are often termed as sonotrodes.

The right hand end of the housing 12 carries a deflecting head generally shown at 28. The deflecting head comprises a deflector housing 30, the exterior shape of which is similar to a ridge prism. A deflecting channel 32 is formed in the deflector housing 30, the central axis of which extends along a quarter of a circle. The transversal cross section of the deflector channel is circular, the cross sectional area continuously diminishing from the inlet opening of the deflector channel 32, which in the drawings is the left hand opening and which is positioned in the vertical plane, towards a lower outlet opening of the deflector channel 32, which in the drawings is oriented in horizontal direction.

The ends of the deflecting passageway 32 are sealed by metal diaphragms 33, 34, which e.g. can be thin steel diaphragms.

A volume 35 of liquid, which is a good sound conductor, is contained in the deflecting passageway 32 in fluid tight manner. Preferably this liquid is a metal, which at ambient temperature or a temperature being slightly above room temperature (40–100°) is in the liquid state, e.g. quicksilver or a low melting nickel alloy or comprises inherently solid or semi-solid or gel-type media, which become liquid when exposed to ultrasonics. Alternatively degassed nonmetal liquids can be used, e.g. degassed water or degassed silicone oil. Still alternatively highly compressed gases may be contained in the deflector channel 32 in fluid tight manner, the pressure of which may be e.g. about 50 atm.

The left hand diaphragm 33 as seen in the drawings is connected to the free end of the amplifying member 28, the metallic diaphragm 34 carrying a dental tool 36, which in accordance with FIGS. 1 and 2 has rod shaped geometry.

In view of exchanging the tool 36, a mounting member 38 may provided on the metallic diaphragm 34 in accordance with FIG. 2, into which the tool 36 is screwed.

In FIG. 3 H designates the axis of handpiece 44, which is also the axis of the vibration generator 16. W designates the axis of the tool 36. These two axis extend in perpendicular directions and due to this fact the hand piece 44 allows for the same ergonomic operating conditions as a conventional mechanical angled hand piece. The deflecting head 28 provides for deflection of the ultrasonic vibrations produced by the vibration generator 16 towards the tool 36.

The hand piece described above operates as follows:

Ultrasonic energy, which is generated by the vibratory system comprising the ultrasonic transducer 18 and the mass members 22, 24 is transferred to the metallic diaphragm 33 via the amplifying member 26 so that its amplitude is increased. The respective essentially sinusoidal movement of the metallic diaphragm 33 schematically shown in FIG. 4 at 40 and having the amplitude "a" induces respective pressure waves in the volume of liquid 35. The metallic membrance 34 is driven by these pressure waves correspondingly, the amplitude being again increased in accordance with reduction of the cross section of the deflector channel 32. The essentially sinusoidal movement of the metallic diaphragm 34 is shown at 42 (amplitude "A"). This movement is transferred to the tool 36 and can serve for removal of material, as will described in more detail below refering to FIG. 3.

It is to be noted, that the vibration amplitudes shown at 40 and 42 are not shown up to scale with respect to the dimensions of the deflecting head 28. Actually, the vibration amplitudes "A" of the tool are in the region of about 2 to 50 μm.

As may be seen from FIG. 3 an angled hand piece 44, which is used for removal of dental material has the same structure as the hand piece 10 shown in FIG. 1 as far as the generation of ultrasonics and deflection of the ultrasonics is concerned. Thus respective components have the same reference numerals affixed thereto. In addition a discharge tube 46 is provided at the end of the housing, for dispensing an abrasive treatment medium 48. The discharge tube 46 is connected to the feed side of a pump 50, which draws the abrasive treatment medium from a mixing vessel 52.

In a modified embodiment an anular discharge nozzle ramp surrounding the tool 36 may be used instead of the discharge tube 46 or together with the latter, which via a plurality of nozzles oriented towards the forward end portion of the tool 36 discharges abrasive treatment medium, preferably to the vicinity of the upper end of the tool.

A supply 54 of mixture contained in the mixinig vessel 52 consists of water, in which large abrasive particles 56, medium size abrasive particles 58 and fine abrasive sealing particles 60 are distributed. These different particles are schematically identified by points, small circles and small triangles, respectively.

The large abrasive particles 56 have a diameter essentially corresponding to the total stroke of the ultrasonic vibrations of the tool 36, which thus amounts to about 2A. Actually the diameters for the large abrasive particles are thus smaller than 100 mμ. The large abrasive particles 56 have a surface including a large number of edges, which is obtained by crushing of grinding of hard material. Thus these particles have goods cutting characteristics. The material of the large abrasive hard grains is selected in view of the respective application. In order to achieve high removal rates silicon carbide materials have proven to be good, good results being obtained with particle sizes between 50 and 80 μm.

The smaller abrasive particles 60 are useful in slower removal and thus in finishing the surface treated. Their diameter can be roughly chosen to be about half or one third of the diameter of the large abrasive particles 56. Also one can choose for these abrasive particles materials, which tend less to formation of strong cutting edges than silicon carbide materials. Examples for such materials are e.g. alumina ceramic materials. In practical work e.g. alumina ceramic particles having the shape of small plates or small disks and having a diameter of about 25 μm have proven to be good, these particles also excelling by hydrophilic properties of their surface. Hydrophilic surfaces of particles are advantageous in view of making stable slurries in water which can be well handled.

The sealing particles 60 are of small diameter. Their diameter is chosen in view of the diameter of small dentin channels of the dental material which are to be closed by the sealing particles 60 as will be described in more detail below. In practical applications the diameter of these sealing particles is below 3 μm, preferable at about 1 μm. Suitable materials for the sealing particles 60 are especially again alumina ceramic materials. In the production of the sealing particles care is taken to obtain a surface having sharp edges. One reason for this is to give these particles still useful abrasive properties in spite of their small diameter, since these particles should also contribute to removal of material; another reason for this is to obtain optimum reliable mechanical engagement of the sealing particles to the ends of the small dentin channels and to surface roughnesses of the surface of the treated cavity. Thus the sealing particles form adhering points to which the filling material may cling and effectively adhere.

As to the mixing ratios of the large abrasive particles 56, the smaller abrasive particles 58 and the sealing particles 60 reference to the explanations given in the introductory part of the specification is made.

The above information relating to the particle sizes relates to the desired sizes of particles in applications, where removal of material is desired. If the particles are made from brittle material, which disintegrates when exposed to ultrasonics, the size of the particles found in the discharged treatment medium may be larger, provided disintegration of these particles at the working site will result in the desired particles sizes.

In view of obtaining a high removal rate it is desirable that the large abrasive particles 56, the medium size abrasive particles 58 and the fine abrasive sealing particles 60 each show only a small standard deviation of the grain size from a desired average diameter.

A mixing rod 62 made from magnetic material is rotated in the mixing vessel 52 by means of a rotating field produced by a solenoid coil 64.

In the lower right hand portion of FIG. 3 the coronal portion 64 of a tooth 66 and its enamel layer 68, its dentin volume 70 and its tooth cavity 72 is shown. Small diameter dentin channels 74 extend from the tooth cavity 72 through the dentin volume 70 up to the enamel layer 68.

A recess 76 has been produced in the tooth 66 starting from the occlusal surface 66 and extending into the dentin volume 70 penetrating the enamel layer 68. Removal of the respective amount of material has been effected by urging the lower end face and the lateral surfaces of the tool 36 towards the dental enamel material and the dentin material, respectively, while simultaneously discharging abrasive treatment medium 48 from the discharge tube 46 and simultaneously supplying ultrasonics to the tool 36. In doing so the vibrating surface of the tool imparts to the abrasive particles a high velocity and when these particles impinge onto the opposing surface of the material they will detach therefrom small fragments. This kind of material removal is gentle and does not result in major damaging of tissues, particularly fractures. By corresponding control of the tool in the three coordinate directions and by rotating the hand piece about the axis corresponding to the coordinate directions (these movements are symbolically shown at 98), the dentist can produce the respectively required tooth cavity.

FIG. 3 shows the situation found after preparation of the cavity has been completed. One recognizes that the ends of the small dentin channels 74, which have been opened by preparing the cavity, have been closed by some of the small sealing particles 60. By this fact the permeability of the dentin volume being adjacent to the cavity is reduced in the sense of an isolating layer functioning as a pulp protection.

The catering of a larger carious dental defect will now be described referring to FIGS. 4 to 9.

In a first step shown in FIGS. 4 and 5 a lateral carious region of the tooth is removed using a first shaping tool 80 which is fixed to the deflecting head 28. The cross sectional view of this tool has the form a curved trapezoid, while the axial section of the tool has the shape of a wedge. By mere axial feeding of the shaping tool 80, which receives ultrasonics via the deflecting head 28, while simultaneously supplying abrasive treatment medium 48, the carious rim portion of the tooth has been removed. In doing so a recess 82 has been formed in the tooth 66, the shape of which is complementary to the exterior shape of the shaping tool 80. At the same time the edges of the cavity can be definitely shaped, e.g. by forming a partial edge chamfer.

In a second step, which is shown in FIGS. 6 and 7, a central recess 84 is formed in the tooth 66, the edge contour of which has about the shape of the cipher "8" oriented in horizontal direction. To this end a further shaping tool 86 is fed in axial direction, which is of corresponding cross section. Again abrasive treatment medium 48 is supplied, which will enter between the exterior surface of the shaping tool 86 and the dental material.

It may be seen from FIG. 8 that subsequent to the forming of the two recesses 82 and 84 a first shaped filling member 88 has been inserted into the recess 82, which consists of dental replacement material and the circumferential shape of which corresponds to that one of the shaping tool 80. The shaped member 88 is connected to the dental material by means of a joint composite layer 90. The upper end face of the shaped filling member 88 has been machined using a treatment tool, which actually can be similar to the one shown in FIG. 1, such that it is an image of the original occlusal surface.

A further shaped filling member 92 is just being inserted into the central recess 84. The exterior contour thereof corresponds to the exterior contour of the shaped tool 86. Between the exterior surface of the shaped filling member 92 and the wall surfaces of the recess 84 a further joint composite layer 94 is shown, which has not yet cured. Ultrasonics is now supplied to the upper end of the shaped filling member 92 using a pressing tool 96, which now is mounted on the deflecting head 28 of the hand piece 10. Thus insertion of the shaped filling member 92 into the recess 84 is assisted, since the viscosity of the joint composite material is reduced by the vibration. This way of inserting the shaped filling member is advantageous in view of joint composite layers or adhesive layers, the thickness of which is as small as possible.

FIG. 8 shows the standard shaped filling member 92, which has been taken from a supply of the dentist to be used in recesses created using the shaped tool 86, the shaped filling member having is original geometry. After curing of the joint composite layer 94 those portions of the shaped filling member 92 projecting beyond the occlusal surface must be removed so that the end face of the shaped filling member 92 being formed again images the original occlusal surface. The respective contours have been indicated in FIG. 9 by narrow lines.

In the description of the restoring phase of catering described above referring to FIG. 8, for the sake of better explanation of the invention it was submitted that the first shaped filling member 88 is first inserted and is fixed in place by composite material, its upper end face then being machined in accordance with the desired geometry of the occlusal surface, the shaped filling member 92 then being inserted into the cavity. It is to be understood, that in such proceeding the composite layer being between the two shaped filling members is applied only when the shaped filling member 92 is inserted so that the two shaped filling members are well interconnected.

In practical work one will generally proceed such that the two shaped filling members 88 and 92 are inserted into the cavity in a common step using composite material and that machining of the upper end faces of the two shaped filling members for providing the desired geometry of the occlusal surface is also carried out in a common step.

FIGS. 10 and 11 show the use of ultrasonic tools in the preparation of tooth stumps for subsequent application of a crown (right hand side: flute preparation; left hand side: preparation of a chamfered shoulder). This machining is again carried out under simultaneous supply of an abrasive treatment medium 48.

The left hand portions of FIGS. 10 and 11 show a tool 98, the vertical cross section of which has the shape of an rectangle, the transversal section of which has the shape of a curved flat rectangle having rounded edges. The curvature of the cross section is chosen in view of the tooth curvature prevailing in the region to be treated. For practical work the dentist disposes of a plurality of such treatment tools of different curvature, which may be chosen from a set of tools.

As may be seen from FIG. 10, the lower end face 100 of the tool 98 is downwardly sloped so that this tool will produce a vertical lateral surface 102 on the tooth stump, which at the lower end is limited by a downwardly and outwardly sloped flute 104.

It is to be noted that the geometry of the shape produced can show different combinations as to the horizontal diameter and the vertical diameter: the flute can be produced with the smaller diameter and the downwardly sloped shoulder can be produced with the larger diameter.

The tool 106 shown in the right hand portion of FIGS. 10 and 11 is similar to the tool 98, however, it has only a smaller circumferential extension so that it can be generally used for treatment of tooth stumps of extremely different circumferential curvature. The lower end face 108 of the tool 106 is e.g. stepped: it comprises a portion of the end face being perpendicular to the axis of the tool and a succeeding downwardly sloped portion of the end face. Thus the tool 106 will produce on the tooth stump again a vertical lateral face 110 and an outwardly and downwardly sloping chamfer 112, a horizontal shoulder 114 being produced in addition, which is located between the chamfer 112 and the lateral surface 110.

FIG. 12 illustrates the gentle removal of material, particularly supragingival and subgingival dental tarter, root concrements and/or plaque at the cervical end of dental roots 116, 118. A first tool 120 has a shaft 122, which may be of similar appearance as the shaft of the tool 106, and an extended work portion 124 is arranged at the lower end of the shaft 122, which generally has the shape of a planting shovel thus being curved in circumferential direction in accordance with the curvature of the dental root 116. The tool 120 has been inserted into a gum pocket 126, which using a syringe 128 has been filled with treatment medium 130. The latter comprises a liquid base material of higher viscosity, wherein again abrasive particles 132 have been distributed and which additionally may comprise, if desired, chemical etching agents and/or germicidal substances.

In a modified process one may also use a treatment medium 130 not containing abrasive particles.

Furthermore it should be noted that the tools 120 and 134 need not have a geometrically defined cutting edge and in so far differ from conventional curets.

The right hand portion of FIG. 12 shows a tool 134 used for removal of dental tarter for treatment of the exterior surface of the dental root 118. This tool has the shape of golf bat or hockey bat. The tool 134 thus includes a shaft 136 carrying a narrow working portion 138 extending in transversal direction. The tool 134 is well suited for treatment of longitudinally curved dental roots or of dental roots having surfaces being concavely curved in circumferential direction.

The left hand portion of FIG. 13 shows a tool 140 (ultrasonic scalpel) which is used for removal of soft tissue, particularly tooth gum or for preparation of soft tissue incisions. A shaft 142 carries a transversal work portion 144 made from a material which will transform ultrasonic energy into heat. A suitable such material is e.g. a compound material comprising two or more different layers of material. Respective examples are bimetallic strips of material or metals having a ceramic coating. Examples for materials showing high interior volume friction are stainless steels. The tool 140 thus works as a ultrasonic cauter and can produce in the tooth gum shown at 146 incisions in precisely controllable manner, cut off parts of the tissue or cauterize vessels.

The right hand portion of FIG. 13 shows a bone preparation tool 148 for removal of bone material 150. A rod shaped shaft 152 carries an e.g. spherical work portion 154. In a modified tool the work portion 154 may have the form of a V-shaped or pyramidal chisel tip. Preferably the tool 148 shown in the right hand portion of FIG. 13 is again used simultaneously supplying an abrasive treatment medium 48.

FIG. 14 shows a tool 156 useful in the preparation of a dental tooth channel 158. The latter has already been opened in the conventional way or using a tool described above with reference to FIGS. 1 through 7 and has been widened mainly using conventional tools. The tool 156 is used for gentle final treatment of the dental root channel 158. To this end it has been given a transversal cross section corresponding to the shape of a rectangle having rounded edges or to the shape of an oval, the transversal cross section diminishing towards the free end of the tool 156. Seen in longitudinal direction the tool 156 has the shape of a slightly curved wedge.

The tool 156 has been selected from a set of tools, wherein the invididual geometry of the tools reflects the average standard geometries (shape, size, diameter) of dental root channels of the different teeth and groups of teeth, respectively.

In a modification of the embodiment shown in FIG. 14, the tool 156 used for preparing a dental root channel can also be provided with a rated break point or separating point marker so that that portion of the tool being complementary to the treated dental root channel can be anchored in the treated root channel to form a restoring member after breaking of the rated break point or severing at the separation marker. This portion of the tool 156 which has the form of a pin like shaped filling member can then be used as an anchoring member for built-up members. Suitable materials for such tools are ceramic materials, metals used for making dental prosthesis or implants as well as plastics materials.

The right hand portions of FIGS. 14 and 15 show a dental root channel 160 which has not been prepared.

FIG. 16 shows an ultrasonic teeth preparation apparatus which is very similar to the one shown in FIG. 3. Functionally equivalent components have again the same reference numerals affixed thereto.

The deflecting head 28 now comprises a ring member 162, which has been designed as to its material and as to its geometry such that is has four maxima of vibration which are spaced by 90° in circumferential direction and lie in portions 162a–162d of the ring member as indicated in FIG. 17. The end of the amplifying member 26 is coupled to that one of the maxima of vibration being located in the portion 162a of the ring member; that one of the vibration maxima which is spaced in downward direction by 90° with respect to the axis of the vibration generator 16 and lies in portion 162d of the ring member is connected to the tool 36. The ring member 162 thus provides for an angular deflection of the ultrasonic energy without amplification of the amplitude. In a direction being perpendicular to the drawing plane, i.e. in axial direction, the ring member 162 is sufficiently dimensioned to warrant that its modes of vibration are pure breathing movements and do not or only to an negligible amount comprise torsional components in circumferential direction.

If the ring member 162 is designed so as to have three maxima of vibration, one can obtain an angle included between the axis H of the hand piece and the axis W of the tool (deflecting angle) corresponding to 120°. With n maxima of vibration one can realize deflecting angles of 360°/n as well as integral multiples thereof.

If intermediate angles are desired, these can be obtained by varying the thickness or the axial extension of the wall of the ring member in circumferential direction, since in such case the nodes of vibration are not equally distributed in circumferential direction.

In a modification of the embodiments described above an asymmetric design of the ring member can be adopted in such manner that the portion of the ring member providing the driving movement shows a greater amplitude than the one found in the driven portion of the ring member. In such case the ring member does not any longer show full rotational symmetry, e.g. it is formed with a circumferentially varying thickness of its wall or its axial extension.

In accordance with a further modification in such cases, where the full amplitude of the vibration produced by the vibration generator 16 is not required at the tool, the tool 36 may be also connected to a ring portion of the ring member 162 lying between a maximum of vibration and a node of vibration.

From FIG. 17 it may also be seen that at a moment, when the vibration generator will exert a pushing force onto the portion 162a of the ring member, a pushing force is exerted onto the tool by the portion 162d of the ring member. Power transfer from the vibration generator to the tool is thus obtained without a phase shift.

In the preparation apparatus shown in FIG. 16 the tool 36 is hollow and is connected by means of a hose 164 to the output of a second pump 166 drawing abrasive treatment medium 170 from a supply vessel 168. The treatment medium in practical work again consists of water, large abrasive particles 172 and in the considered embodiment furthermore of sealing particles 174 for closing the small dentin channels 74. The fact that the treatment medium 170 does contain no praticles corresponding to the medium size abrasive particles 58 is meant to indicate that the treatment medium 170 may differ from the treatment medium 48. Such difference may also pertain to further additions to the treatment medium, which serve for control of the viscosity or have medicinal function.

A double arrow shown in the suction line of the pump 166 indicates that this pump can also be used for evacuating used treatment medium through the tool 36.

FIG. 18 shows a further embodiment of the invention, wherein the shaping tool is formed by the shaped filling member later be connected to the dental material.

A mounting member 178 is moulded into the upper end of a shaped filling member 176, the geometry of which essentially corresponds to the geometry of the shaping tool 86. The mounting member 178 mates the mounting part 38. The shaped filling member 176 has an upper portion formed with a rated break point 180. Thus after sinking in the shaped filling member 176 (simultaneously supplying an abrasive treatment medium as has been described above) the mounting member 180 can be broken away or severed by a blow. The shaped filling member 166 will then be adhesively connected to the dental material as has been described above and the upper portion of the shaped filling member 176 is machined for reforming the occlusal surface.

As has been pointed out above referring to FIG. 14, already, a further example for a shaped filling member simultaneously being used as a shaping tool is a tool for the treatment of dental root channels as shown in FIG. 14.

Materials suited for making tools which also represent shaped filling members are metal alloys, e.g. titanium alloys, as well as oxide type or non-oxide type ceramic materials, particularly alumina ceramics or silicon-carbide sintered materials.

What is claimed is:

1. An apparatus for ultrasonic preparation of at least one of human and animal hard and soft tissue and dental and bone replacement materials, comprising:

an ultrasonic vibration generator (16), a tool (36, 80, 86, 96, 98, 106, 120, 134, 140, 148, 156, 176) driven thereby, and a sound deflecting head (28) arranged between said vibration generator (16) and said tool and having a driven input (33, 162a) that is movable in a direction parallel to a longitudinal axis of said vibration generator (16) and a driving output (34, 162d) that is movable along an axis cooperating with said longitudinal axis of said vibration generator (16) to define an angle different from zero degrees, in which said tool is connected to said driving output (34, 162d) of said deflecting head (28).

2. The apparatus according to claim 1, in which said tool vibrates in a direction parallel to a longitudinal axis of said tool.

3. The apparatus according to claim 2, in which said deflecting head (28) comprises a vibrating member (162) having a resonant frequency coinciding with an operating frequency of said vibration generator (16), vibration induced in said vibrating member (162) has a plurality of circumferentially spaced maxima of vibration, and said vibrating member (162) has a first ring portion (162a) associated with a first maximum of vibration that is coupled to said vibration generator (16) and a second ring portion (162d) associated with a different maximum of vibration that is coupled to said tool.

4. The apparatus according to claim 3, in which said vibrating member (152) is selected from the group consisting of a ring, a sleeve, and a hollow sphere.

5. The apparatus according to claim 1, in which said deflecting head comprises a deflector housing (30) having a deflector channel (32) containing a volume of at least one liquid or gas.

6. The apparatus according to claim 5, in which said deflector channel (32) has ends enclosed in a fluid tight manner by at least one of a diaphragm (33, 34) and a movable plunger.

7. The apparatus according to claim 6, in which said at least one diaphragm (33, 34) and plunger is oriented perpendicular to said longitudinal axis of said vibration generator (16) and a longitudinal axis of said tool (36), respectively.

8. The apparatus according to claim 7, in which said diaphragm (33, 34) has a thickness that decreases from a periphery of said diaphragm that is connected to said deflector housing (30) towards a center of said diaphragm.

9. The apparatus according to claim 8, in which said diaphragm (33, 34) is made of at least one metal and metal alloy.

10. The apparatus according to claim 5, in which said volume of liquid (35) contained in said deflector channel (32) has low viscosity at least when exposed to ultrasonics.

11. The apparatus according to claim 10, in which said volume of liquid (35) is selected from the group consisting of quick silver, water, alcohol, alcohol-water mixtures, silicone oils, and liquid phase nickel alloys.

12. The apparatus according to claim 1, in which an angle between said longitudinal axis of said vibration generator (16) and a longitudinal axis of said tool is between approximately 60 degrees and 120 degrees.

13. The apparatus according to claim 12, in which said angle between said longitudinal axis of a vibration generator (16) and said longitudinal axis of said tool is 90 degrees.

14. The apparatus according to claim 1, in which said vibration generator (16), said deflecting head (28), and said tool comprise an overall system that oscillates at resonance frequency.

15. The apparatus according to claim 1, in which said tool comprises a negative model of a shaped filling member (88, 92, 176) that is made from tissue replacement material, and said tool and said deflecting head (28) are formed such that said tool can be sunk while oscillating at least partially into material to be treated.

16. The apparatus according to claim 15, further comprising a set of different tools designed for different sizes of teeth and different minimum preparation depths.

17. The apparatus according to claim 16, in which said set of different tools are specific for replacement material used and represent negative models corresponding to different shaped filling members.

18. The apparatus according to claim 17, further comprising a set of shaped filling members that are provided in same shapes and size gradations as said tools.

19. The apparatus according to claim 18, in which said shaped filling members are selected from a group consisting of ceramic material, polymer composite material, and metal, and have surfaces that are at least partially coated with fixing materials.

20. The apparatus according to claim 19, in which said surfaces are positively connected by means of at least one of force and geometry.

21. The apparatus according to claim 15, further comprising a shaped filling member to be inserted in a tissue cavity in which said tool and said shaped filling member to be inserted into a tissue cavity are both formed by a shaped filling member (156, 176) comprised of a biocompatible hard material.

22. The apparatus according to claim 21, in which said shaped filling member (156, 176) is comprised of a material selected from oxide-type ceramic material, non-oxide type ceramic material, and metallic material.

23. The apparatus according to claim 21, in which said shaped filling member (156, 176) comprises a mounting portion (178) connectable to said driving output member (34, 162b) of said deflecting head (28) and connected to a portion (176) of said shaped filling member to be inserted into a tissue cavity by means of a rated break point (180).

24. The apparatus according to claim 23, in which said mounting portion (178) is connected to said inserted portion of said shaped filling member by at least one connection selected from screwing, wedging, and soldering.

25. A method for ultrasonic preparation of at least one of dental and bone replacement materials comprising the steps of obtaining and using a tool according to claim 15.

26. A method for ultrasonic preparation of at least one of human and animal, hard and soft tissue, comprising the steps of obtaining and using a tool according to claim 15.

27. The apparatus according to claim 1, in which said tool comprises a work portion (144) of a material that heats when exposed to ultrasonics.

28. The apparatus according to claim 27, in which said work portion (144) is internally frictionally heated.

29. The apparatus according to claim 28, which said work portion (144) comprises a plurality of different material layers.

30. The apparatus according to claim 1, comprising at least one means (46, 50, 52, 164, 166, 168) supplying abrasive treatment medium (48, 170) to said tool.

31. The apparatus according to claim 30, in which said abrasive treatment medium (48, 170) comprises small abrasive sealing particles (60) having an average diameter smaller than approximately 5 $\mu$m.

32. The apparatus according to claim 31, in which said average diameter of said abrasive sealing particles (60) is approximately 1 $\mu$m.

33. The apparatus according to claim 31, in which said abrasive sealing particles comprise sealing particles (60) selected from the group consisting of sealing particles of oxide-type, silicate-type, carbide-type, nitride-type, and polymer-containing materials.

34. The appartus according to claim 31, in which said abrasive sealing particles have surfaces that are apt to establish an at least partly chemical compound with at least one of silanes and polymers.

35. The apparatus according to claim 31, in which said abrasive sealing particles are apt to be at least partly integrated into a gel when exposed to jellying joint filling material at least partly containing an acid.

36. The apparatus according to claim 31, in which one unit volume of said abrasive sealing particles is used with two to twenty volumes of abrasive particles.

37. The apparatus according to claim 36, in which one unit volume of said abrasive sealing particles is used with ten unit volumes of abrasive particles.

38. apparatus according to claim 31, in which said abrasive treatment medium includes abrasive particles (56) having a diameter that approximately corresponds to an overall stroke of said ultrasonic vibration tool.

39. The apparatus according to claim 38, in which one unit volume of abrasive particles is used with three to thirty unit volumes of liquid.

40. The apparatus according to claim 39, in which one unit volume of abrasive particles is used with five to twenty unit volumes of liquid.

41. The apparatus according to claim 40, in which one unit volume of abrasive particles is used with ten unit volumes of liquid.

42. The apparatus according to claim 31, in which said abrasive sealing particles have at least one of a hydrophilic surface and a hydrophilic surface coating.

43. The apparatus according to claim 30, in which said abrasive treatment medium (130) comprises at least one gel.

44. The apparatus according to claim 43, in which said abrasive treatment medium (130) has modified viscosity.

45. The apparatus according to claim 44, in which said modified viscosity is realized by addition of aerosil and a gelling base substance.

46. The apparatus according to claim 43, in which said abrasive treatment medium is at least partly transferred into a liquid state when exposed to ultrasonics.

47. The apparatus according to claim 43, in which a base component of said abrasive treatment medium (130) is selected from at least one of glycerin gel, a one to ten percent chloral-hexidine gel and gelatin.

48. The apparatus according to claim 30, further comprising means for supplying treatment liquid (48) to an exterior surface of said tool.

49. A method of ultrasonic preparation of at least one of dental and bone replacement materials comprising the steps of obtaining and using an abrasive treatment apparatus according to claim 30.

50. A method for ultrasonic preparation of at least one of human and animal, hard and soft tissue, dental and bone replacement materials comprising the steps of obtaining and using an abrasive treatment apparatus according to claim 30.

51. The apparatus according to claim 1, in which said tool at least partially comprises a hollow member and is connected to means for supplying abrasive treatment medium (164, 166, 168).

52. The apparatus according to claim 1, in which said tool (96) comprises at least one convex vibrating head.

53. The apparatus according to claim 1, in which said tool has a curved transversal cross-section.

54. The apparatus according to claim 1, in which said tool comprises at least one of a flute-shaped work portion (124) and a shovel-shaped work portion (124).

55. The apparatus according to claim 1, in which said tool has a free end-face (100, 108) having a portion inclined with respect to a longitudinal axis of said tool.

56. The apparatus according to claim 55, in which said free end-face (108) of said tool (106) comprises a portion extending perpendicularly to said longitudinal axis of said tool.

57. The apparatus according to claim 1, in which said tool has a free end-face (100, 108) having a portion curved in the sense of a flute.

58. The apparatus according to claim 1, in which said tool (134) comprises a shaft and a transversal work portion (138) connected to a free end of said shaft.

59. The apparatus according to claim 1, in which said tool (148) comprises a chisel tip (154).

60. The apparatus according to claim 1, in which said tool has a geometry corresponding to a geometry of a dental root channel (158).

61. The apparatus according to claim 1, in which said tool has an end portion that vibrates in a direction transversal to a longitudinal axis of said tool.

62. A method for ultrasonic preparation of at least one of human and animal, hard and soft tissue, dental and bone replacement materials comprising the steps of obtaining an apparatus according to claim 1 and using said apparatus in a dental procedure.

63. A method for treatment of soft tissue comprising the steps of obtaining and using an apparatus according to claim 1.

64. A method for ultrasonic preparation of at least one of dental and bone replacement materials comprising the steps of obtaining and using an apparatus according to claim 1.

65. A method of forming a cavity in a tooth comprising the steps of obtaining and using an apparatus according to claim 1 to form said cavity.

* * * * *